US008187802B2

(12) United States Patent
White et al.

(10) Patent No.: US 8,187,802 B2
(45) Date of Patent: May 29, 2012

(54) CELL LINES USEFUL FOR ASSESSING MODULATION OF AUTOPHAGY

(75) Inventors: Eileen White, Princeton, NJ (US); Anne Marie Strohecker, New York, NY (US); Robin Mathew, Monroe, NJ (US); Cristina Karp, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/622,410

(22) Filed: Nov. 19, 2009

(65) Prior Publication Data

US 2010/0233730 A1 Sep. 16, 2010

Related U.S. Application Data

(60) Provisional application No. 61/116,085, filed on Nov. 19, 2008.

(51) Int. Cl.
 *C12Q 1/00* (2006.01)
 *C12N 5/00* (2006.01)
 *C12N 5/07* (2006.01)
(52) U.S. Cl. ............................. 435/4; 435/325; 435/354
(58) Field of Classification Search ........................ None
 See application file for complete search history.

(56) References Cited

PUBLICATIONS

Stoffler et al. 1999. Current Opin in Cell Biol. 11:391-401.*
Bjorkoy et al. 2005. J. Cell Biol. 171:603-614.*
Mathew et al. 2007. Genes Dev. 21:1367-1381).*
Komatsu et al 2007. Cell. 131:1149-1163.*
Degenhardt et al. (2006), Autophagy promotes tumor cell survival and restricts necrosis, inflammation, and tumorigenesis, Cancer Cell 10: 51-64.
Degenhardt et al., (2002) Bax and Bak independently promote cytochrome C release from mitochondria, J Biol Chem 277: 14127-14134.
Ding et al., (2007), Linking of autophagy to ubiquitin-proteasome system is important for the regulation of endoplasmic reticulum stress and cell viability, Am J Pathol 171: 513-524.
Jin, S., and White, E. (2007), Role of autophagy in cancer: management of metabolic stress. Autophagy 3: 28-31.
Jin, S., and White, E. (2008), Tumor suppression by autophagy through the management of metabolic stress, Autophagy 4: 563-566.
Karantza-Wadsworth et al., (2007), Autophagy mitigates metabolic stress and genome damage in mammary tumorigenesis, Genes Dev 21: 1621-1635.
Komatsu et al. (2007), Homeostatic Levels of p62 Control Cytoplasmic Inclusion Body Formation in Autophagy-Deficient Mice, Cell 131: 1149-1163.

Levine, B., and Kroemer, G. (2008), Autophagy in the pathogenesis of disease, Cell 132: 27-42.
Lum et al., (2005), Growth factor regulation of autophagy and cell survival in the absence of apoptosis, Cell 120: 237-248.
Mathew et al., (2007), Role of autophagy in cancer, Nat Rev Cancer 7: 961-967.
Mathew et al. (2008), Immortalized mouse epithelial cell models to study the role of apoptosis in cancer, Methods Enzymol, 446: 77-106.
Mathew et al. (2007), Autophagy suppresses tumor progression by limiting chromosomal instability, Genes Dev 21: 1367-1381.
Nelson et al. (2004) Hypoxia and defective apoptosis drive genomic instability and tumorigenesis, Genes Dev 18: 2095-2107.
Mathew et al. (2009), Autophagy suppresses tumorigenesis through elimination of p62, Cell 137: 1062-1075.
Rodriguez et al. (2006), Mature-onset obesity and insulin resistance in mice deficient in the signaling adapter p62, Cell Metab 3: 211-222.
Root et al. (2006), Genome-scale loss-of-function screening with a lentiviral RNAi library, Nature Methods 3: 715-719.
Zatloukal et al. (2002), p62 is a common component of cytoplasmic inclusions in protein aggregation diseases, Am. J. Pathol. 160: 255-263.
Pankiv et al. (2007), p62/SQSTM1 Binds Directly to Atg8/LC3 to Facilitate Degradation of Ubiquitinated Protein Aggregates by Autophagy, The Journal of Biological Chemistry vol. 282, No. 33, pp. 24131-24145.
Klionsky, D. (2007), Autophagy: from phenomenology to molecular understanding in less than a decade, Nat Rev Mol Cell Biol 8,931-937.
Moscat et al. (2006), Signal integration and diversification through the p62 scaffold protein, Trends in Biochemical Sciences vol. 32, No. 2, pp. 95-100.
Filimonenko et al. (2007), Functional multivesicular bodies are required for autophagic clearance of protein aggregates associated with neurodegenerative disease, The Journal of Cell Biology, vol. 179, No. 3, pp. 485-500.
Duran et al. (2008), The Signaling Adaptor p62 Is an Important NF-kB Mediator in Tumorigenesis, Cancer Cell 13: 343-354.
Wooten et al. (2008), Essential Role of Sequestosome 1/p62 in Regulating Accumulation of Lys63-ubiquitinated Proteins, The Journal of Biological Chemistry vol. 283, No. 11, pp. 6783-6789.
Bjorkoy et al (2005), p62/SQSTM1 forms protein aggregates degraded by autophagy and has a protective effect on huntingtin-induced cell death, The Journal of Cell Biology, vol. 171, No. 4, pp. 603-614.

* cited by examiner

*Primary Examiner* — Shulamith H Shafer
(74) *Attorney, Agent, or Firm* — Fox Rothschild LLP

(57) ABSTRACT

Methods for screening for modulators of autophagy are disclosed. Methods for identifying genes whose expression inhibits autophagy, as well as genes whose expression promotes autophagy, are disclosed. Also disclosed are methods for identifying compounds that stimulate autophagy, as well as compounds that inhibit autophagy. Cell lines that may be used in the methods of identification are also disclosed.

9 Claims, 12 Drawing Sheets

CELL LINES USEFUL FOR ASSESSING MODULATION OF AUTOPHAGY

CROSS-REFERENCE TO RELATED APPLICATION

This application claims benefit of U.S. Provisional Application No. 61/116,085, filed Nov. 19, 2008, the disclosure of which is hereby incorporated by reference herein, in its entirety.

GOVERNMENT SUPPORT

The present application was supported in part by the National Institutes of Health under Grant Nos. R37 CA53370 and RO1 CA130893 and the Department of Defense under DOD W81XWH06-1-0514 and DOD W81XWH05. The government has certain rights in the invention.

BACKGROUND OF THE INVENTION

Macroautophagy (autophagy) is an important mechanism for targeting cellular components including proteins, protein aggregates and organelles for degradation in lysosomes. This catabolic, cellular self-digestion process is induced in response to starvation or stress, causing the formation of double membrane vesicles called autophagosomes that engulf proteins and organelles. Autophagosomes then fuse with lysosomes where the autophagosome and their cargo are degraded. This lysosome-mediated cellular self-digestion serves to recycle intracellular nutrients to sustain cell metabolism during starvation and to eliminate damaged proteins and organelles that accumulate during stress. Although elimination of individual proteins occurs by the ubiquitin-mediated proteasome degradation pathway, the autophagy pathway can eliminate protein aggregates and organelles. Thus, autophagy complements and overlaps with proteasome function to prevent the accumulation of damaged cellular components during starvation and stress. Through these functions, autophagy is an essential cellular stress response that maintains protein and organelle quality control, protects the genome from damage, and sustains cell and mammalian viability.

Autophagy is thought to be controlled by ATG proteins, initially identified in yeast, for which there are mammalian homologues (Levine, B., and Kroemer, G. (2008), Autophagy in the pathogenesis of disease, *Cell* 132, 27-42). ATG proteins are comprised of kinases, proteases, and two ubiquitin-like conjugation systems that likely function in concert with a host of unknown cellular proteins to control autophagosome formation, cargo recognition, engulfment, and trafficking to lysosomes.

In mice, autophagy enables survival of neonatal starvation by preventing energy depletion. Mice with targeted autophagy-deficiency (atg5$^{-/-}$ or atg7$^{-/-}$) in the brain accumulate damaged mitochondria and polyubiquitin-containing protein aggregates, and display neuronal degeneration. Defects in autophagy through liver-specific atg7 deletion in mice similarly results in protein aggregate accumulation, hepatocyte cell death and severe liver injury. These findings support a prosurvival role for autophagy in sustaining cellular metabolism and maintaining protein and organelle quality control by eliminating damaged proteins and organelles that are particularly important during nutrient stress and aging (Levine, B. and Kroemer, G., (2008)).

Autophagy dysfunction is a major contributor to diseases including, but not limited to, neurodegeneration, liver disease, and cancer. Many human neurodegenerative diseases are associated with aberrant mutant and/or polyubiquitinated protein accumulation and excessive neuronal cell death. Neurons of mice with targeted autophagy defects accumulate polyubiquitinated- and p62 containing protein aggregates that result in neurodegeneration. The human liver disease steatohepatitis and a major subset of hepatocellular carcinomas (HCCs) are associated with the formation of p62-containing protein aggregates (Mallory bodies) (Zatloukal, K., et al. (2002), p62 is a common component of cytoplasmic inclusions in protein aggregation diseases, *Am. J. Pathol.* 160, 255-263). Livers of mice with autophagy defects have p62-containing protein aggregates, excessive cell death, and HCC.

Autophagy is also induced by stress and starvation in tumor cells where it predominantly provides a prosurvival function. Metabolic stress is common and autophagy localizes to metabolically-stressed tumor regions. Autophagy has been identified as an important survival pathway in epithelial tumor cells that enables long-term survival to metabolic stress (Degenhardt, K., et al. (2006), Autophagy promotes tumor cell survival and restricts necrosis, inflammation, and tumorigenesis, *Cancer Cell* 10, 51-64; Jin, S., and White, E. (2007), Role of autophagy in cancer: management of metabolic stress. *Autophagy* 3, 28-31; Karantza-Wadsworth, V., et al., (2007), Autophagy mitigates metabolic stress and genome damage in mammary tumorigenesis, *Genes Dev* 21, 1621-1635; Mathew, R. et al., (2007a), Role of autophagy in cancer, *Nat Rev Cancer* 7, 961-967; Mathew, R., et al. (2007b), Autophagy suppresses tumor progression by limiting chromosomal instability, *Genes Dev* 21, 1367-1381). Tumor cells with defined defects in autophagy accumulate p62-containing protein aggregates, DNA damage, and die in response to stress, whereas those with intact autophagy can survive for weeks utilizing the autophagy survival pathway. Thus, autophagy may be required to prevent tumor cell damage and to maintain metabolism. Tumor cells can exploit this survival function to remain dormant only to reemerge under more favorable conditions.

Paradoxically, autophagy defects through allelic loss of the essential autophagy gene beclin1 or through constitutive activation of the autophagy-suppressing PI-3 kinase/mTOR pathway are common in human tumors. Roughly half of human cancers may have impaired autophagy, either due to constitutive activation of the PI-3 kinase pathway or allelic loss of the essential autophagy gene beclin1, rendering them particularly susceptible to metabolic stress and autophagy inhibition (Jin et al., 2007; Jin, S., and White, E. (2008), Tumor suppression by autophagy through the management of metabolic stress, *Autophagy* 4, 563-566).

Analogous to a wound-healing response, chronic tumor cell death in response to stress and induction of inflammation and cytokine production may provide a non-cell-autonomous mechanism by which tumorigenesis is promoted in autophagy-defective cells. Autophagy-defective tumor cells also display an elevated DNA damage response, gene amplification and chromosome instability in response to stress, suggesting that autophagy limits genome damage as a cell-autonomous mechanism of tumor suppression. Possible non-mutually exclusive mechanisms by which autophagy may protect the genome include maintenance of metabolism and ATP levels, reduction of oxidative stress, and elimination of damaged protein and organelles.

The importance of autophagy in cellular garbage disposal is clear, as autophagy is the only identified mechanism for the turnover of large cellular structures such as organelles and protein aggregates. How organelles are recognized and directed to autophagosomes for degradation may involve organelle-specific processes such as mitophagy and ER-phagy that may mitigate oxidative stress emanating from dysfunctional organelles. Damaged proteins that accumulate during stress can be refolded, ubiquitinated and degraded by the proteasome pathway, or aggregated and degraded by autophagy. To direct damaged or unfolded proteins to the autophagy pathway, p62 binds to polyubiquitinated proteins forming protein aggregates by oligomerization and to Atg8/LC3 on the autophagosome membrane to target aggregates to autophagosomes for degradation. Protein aggregation may be a protective mechanism to limit cellular exposure to toxic proteins through sequestration, as well as an efficient packaging and delivery mechanism that collects and directs damaged proteins to autophagosomes. Liver-specific autophagy defects in mice cause accumulation of p62 aggregates, elevated oxidative stress and hepatocyte cell death. Thus, without seeking to be bound by any theory or theories of operation, it is believed that the inability to dispose of p62 aggregates through autophagy may be toxic to normal tissues.

The ATG6/Beclin1-Vps34-ATG8/LC3 complex regulates autophagosome formation; LC3 cleavage, lipidation, and membrane translocation are frequently utilized to monitor autophagy induction. The mechanism by which starvation and stress activate autophagy is controlled in part through the PI-3 kinase pathway via the protein kinase mTOR. Growth factor and nutrient availability promote mTOR activation that suppresses autophagy, whereas starvation and mTOR inactivation stimulate autophagy (Klionsky (2007), *Nat Rev Mol Cell Biol* 8, 931-937). While there are other mechanisms to regulate autophagy, mTOR provides a link between nutrient and growth factor availability, growth control, autophagy, and metabolism.

Autophagy is believed to play an essential role in maintaining protein quality control, while defective autophagy may be involved in the development of diseases including, but not limited to, neurodegeneration, steatohepatitis, and cancer. Therefore, there exists a need for identification of stimulators of autophagy.

Additionally, there exists a need for the identification of inhibitors of the autophagy survival pathway in, for example, cancer cells. Such inhibitors of autophagy could be used in the prevention and/or treatment of cancer.

BRIEF SUMMARY OF THE INVENTION

In certain aspects, the present invention relates to methods of identifying modulators of autophagy. Certain aspects relate to methods of identifying inhibitors of autophagy. Other aspects relate to methods of identifying stimulators of autophagy. Additional aspects relate to methods of identifying genes whose expression affects autophagy.

One aspect of the invention relates to a method comprising the steps of: A) screening an shRNA library using a test cell that expresses an autophagosome marker; (B) subjecting the cell to metabolic stress; and (C) performing analysis on the cell to determine the localization of the autophagosome marker in the test cell.

Another aspect of the present invention relates to a method for identifying inhibitors of autophagy comprising the steps of: (A) contacting a test cell that expresses an autophagosome marker with a compound; (B) subjecting the test cell to metabolic stress; and (C) performing analysis on the test cell to determine the localization of the autophagosome marker in the cell.

In one aspect, the present invention relates to a method comprising: (A) screening an shRNA library using an autophagy-defective test cell expressing a marker of protein aggregation; (B) subjecting the test cell to metabolic stress; and (C) performing analysis on the test cell to determine the level of the marker.

In another aspect, the present invention relates to a method for identifying stimulators of autophagy comprising the steps of: (A) contacting a test cell expressing a marker of protein aggregation with a compound; (B) subjecting the cell to metabolic stress; and (C) performing analysis on the test cell to determine the level of the marker.

Additional aspects relate to cells and cell lines that may be used in certain embodiments of the invention.

Both the foregoing general description and the following detailed description are exemplary and explanatory, and are intended to provide further explanation of the invention as claimed. Other aspects, advantages, and novel features will be readily apparent to those skilled in the art from the following detailed description of the invention.

DETAILED DESCRIPTION OF THE INVENTION

Figure 1:
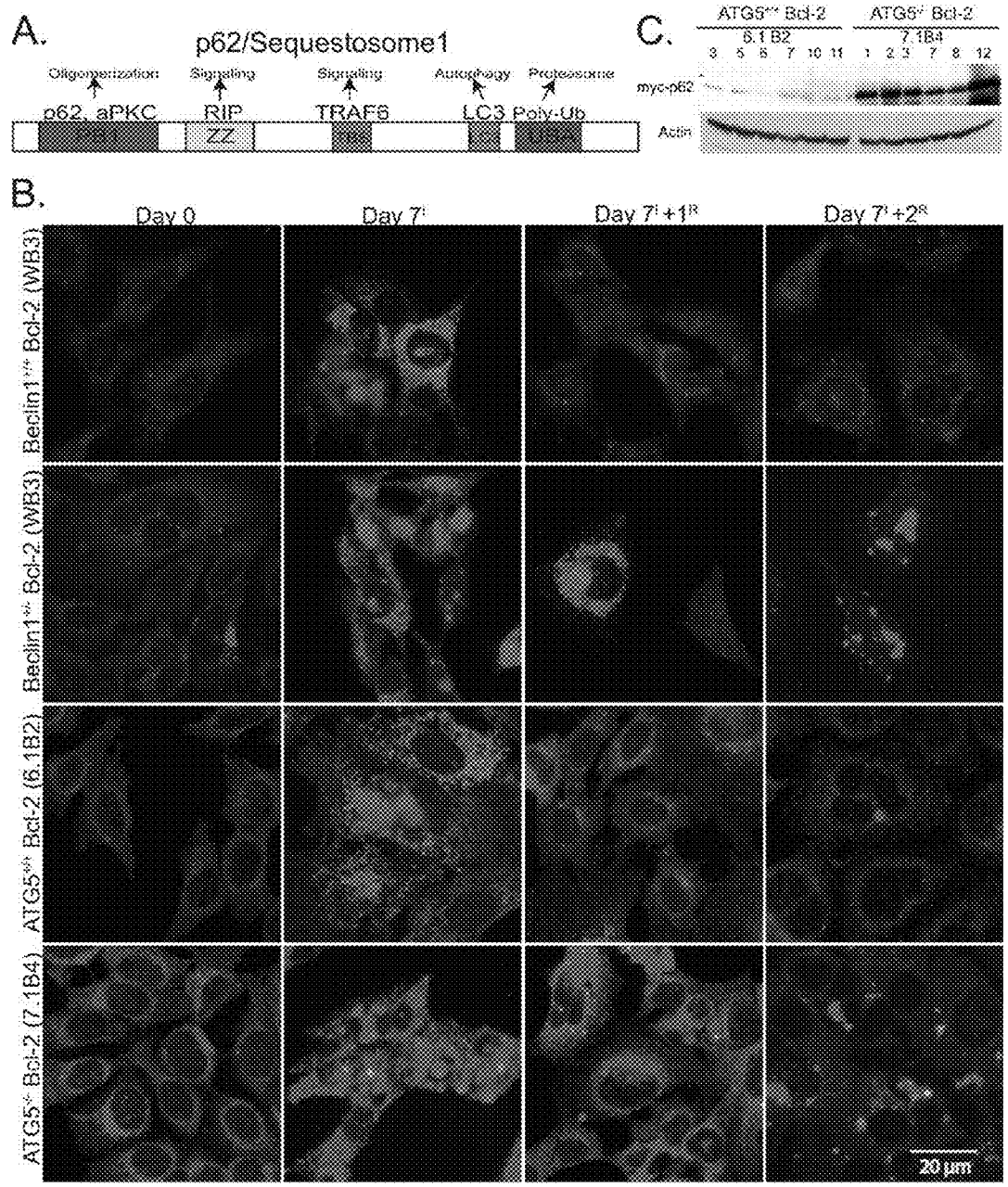
FIG. 1 illustrates elevated and persistent p62 in autophagy-defective tumor cells under metabolic stress. (A) Domain organization of p62 (SQSTM1/Sequestosome 1) illustrating the Phox and Bem1p (PB1) domain that assists in oligomerization and binding to atypical Protein Kinase C (aPKC), the Zinc finger (ZZ) domain that binds to the receptor interacting protein (RIP), the TRAF6 binding site (TBS) involved in NF-κB signaling, the microtubule associated protein light chain 3 (LC3) binding domain that interacts with LC3/ATG8, and the ubiquitin-associated (UBA) domain that binds polyubiquitin. (B) IF of endogenous p62 showing preferential accumulation and persistence of p62 in autophagy-defective cells. Bcl-2 expressing beclin1$^{+/+}$, beclin1$^{+/-}$, atg5$^{+/+}$ and atg5$^{-/-}$ iBMK cells were stained for endogenous p62 under normal growth conditions (Day 0) or following 7 days of metabolic stress (Day 7$^I$) and 1 (Day 7+1$^R$) and 2 (Day 7+1$^R$) days of recovery. (C) Autophagy-defective cells express constitutively higher levels of exogenous myc-p62. Bcl-2 expressing atg5$^{+/+}$ and atg5$^{-/-}$ iBMK cells were transfected with myc-tagged p62 expression vector (pcDNA3-myc-p62) and six independent cell lines of each were evaluated for p62 expression levels by Western blotting with an antibody recognizing the myc epitope tag.

Embodiments of the present invention include methods of screening for modulators of autophagy. In some embodiments, cell-based screens may be used to identify activators and/or inhibitors of autophagy. In certain embodiments, cell-based screens may be used to identify genes whose expression modulates autophagy. Such genes may represent targets for therapeutic intervention in the autophagy pathway.

In one embodiment, the invention provides a method comprising the steps of: (A) screening an shRNA library using a test cell that expresses an autophagosome marker; (B) subjecting the cell to metabolic stress; and C) performing analysis on the cell to determine the localization of the autophagosome marker in the test cell. Certain embodiments include step (D) comparing the localization of the marker in the test cell with that of a control, wherein a lower level of localization of the marker in autophagosomes in the test cell compared to that demonstrated by the control cell indicates knockdown of a gene whose expression induces autophagy.

In another embodiment, the invention provides a method for identifying inhibitors of autophagy comprising the steps of: (A) contacting a test cell that expresses an autophagosome marker with a compound; (B) subjecting the test cell to metabolic stress; and (C) performing analysis on the test cell to determine the localization of the autophagosome marker in the cell. Certain embodiments include step (D) comparing the localization of the marker in the cell with that of a control cell, wherein a lower level of localization of the marker in autophagosomes in the test cell compared to that demonstrated by the control cell indicates that the compound is capable of inhibiting autophagy.

In certain embodiments, cells used in the methods may be apoptosis-defective. In certain preferred embodiments, the cells may be bax$^{-/-}$bak$^{-/-}$.

In certain embodiments, the autophagosome marker comprises EGFP-LC3. In preferred embodiments, the analysis performed comprises image analysis to determine a level of punctate localization of the autophagosome marker.

In another embodiment of the invention, a method is provided comprising the steps of: (A) screening an shRNA library using an autophagy-defective test cell expressing a marker of protein aggregation; (B) subjecting the test cell to metabolic stress; and (C) performing analysis on the test cell to determine the level of the marker. Certain embodiments include step (D) comparing the level of the marker in the test cell with that of a control cell, wherein a lower level of aggregates comprising the marker in the test cell compared to that demonstrated by the control cell indicates the lowered expression of a gene whose knockdown increases aggregate clearance.

Another embodiment is directed to a method for identifying stimulators of autophagy comprising the steps of: (A) contacting a test cell expressing a marker of protein aggregation with a compound; (B) subjecting the cell to metabolic stress; and (C) performing analysis on the test cell to determine the level of the marker. Certain embodiments include step (D) comparing the level of the marker in the test cell with that of a control cell, wherein a lower level of aggregates comprising the marker in the test cell compared to that demonstrated by the control cell indicates that the compound is capable of increasing autophagy.

In certain embodiments, cells used in the methods may be apoptosis-defective. In certain embodiments, the cells may be autophagy-defective. Preferably, cells may have reduced expression of one or more of the Beclin1, Atg5, or Atg7 genes.

In certain embodiments, the marker of protein aggregation comprises p62 protein linked to a label molecule. In preferred embodiments, the label molecule is enhanced green fluorescent protein (EGFP). In certain embodiments, the analysis performed comprises image analysis to determine the level of p62 protein aggregates.

In preferred embodiments of the invention, cells useful in methods for screening for modulators of autophagy include, without limitation, immortalized baby mouse kidney cells.

In certain embodiments, cell-based methods according to the invention may be used for high-throughput screening assays.

It has now been found that metabolic stress caused autophagy-defective tumor cells to preferentially accumulate p62, ER chaperones such as glucose-regulated protein 170 (GRp170), glucose-regulated protein 78 (GRp78), calnexin and protein disulphide isomerases (PDIs), indicative of protein quality control failure. Moreover, autophagy defects caused mitochondrial destruction, elevated oxidative stress and activation of the DNA damage response, which were attributed directly to persistence of p62. The failure to degrade p62 and the resulting cytotoxic effects manifested during stress and recovery with defective autophagy, were partially suppressed by ROS scavengers indicating that persistence of p62 and oxidative stress contributed to cellular damage. This failure to clear p62 following stress in autophagy-defective cells greatly accelerated tumorigenesis, indicating that autophagy is required to prevent p62 accumulation, that if allowed to persist, is sufficient to promote tumor growth. p62 is commonly upregulated in human tumors, suggesting that defective autophagy is a mechanism by which this occurs and that is an oncogenic mechanism.

Inactivation of the autophagy tumor suppressor mechanism is common in tumors, not only through allelic loss of beclin1, but also potentially through indirect mechanisms such as constitutive activation of the PI-3 kinase pathway, which activates mTOR that suppresses autophagy. In tumor cells with Rb and p53 checkpoints inactivated, defects in autophagy impair stress tolerance and amplify genome damage, suggesting that the protective function of autophagy limits genetic instability and suppresses tumor initiation and progression. While not intending to be limited by any theory or theories of operation, it is believed that the increased damage that results from the inability of autophagy-defective cells to manage metabolic stress may facilitate tumor initiation and progression of those cells that do not die. If so, then the tumor suppression mechanism of autophagy is related to how this management of metabolic stress prevents cellular damage.

Evidence from model organism disease models indicates that promoting autophagy with mTOR inhibitors such as rapamycin, and enhancing the clearance of misfolded, damaged or mutated proteins and protein aggregates prevents neurodegeneration, but that there also are mTOR independent means to increase autophagy. Similarly, genetically eliminating the expression of p62 in hepatocytes and preventing p62 accumulation in autophagy-defective atg7$^{-/-}$ hepatocytes dramatically suppresses the phenotype of steatohepatitis. In contrast, neurodegeneration due to expression and accumulation of polyglutamate expansion mutant proteins is greatly exacerbated by allelic loss of beclin1 and defective autophagy. Thus, autophagy may be required to limit the buildup of misfolded, mutated proteins in p62-containing protein aggregates, which leads to cellular deterioration and disease.

Autophagy-defective mouse tissues have low ATP levels and accumulate polyubiquitinated- and p62-containing protein aggregates and abnormal mitochondria, indicating failure of energy homeostasis and protein and organelle degradation. This may be associated with elevated cell death and persistence of dead cells that cannot be engulfed or degraded. It has now been found that accumulation of p62 in response to metabolic stress represents a striking phenotype of autophagy-defective tumors cells with allelic loss of beclin1 or deficiency in atg5, suggesting defective protein quality control is potentially a major contributing factor to tumorigenesis. Thus autophagy appears to be a mechanism by which tumor cells rapidly and efficiently turnover p62.

Figure 4:
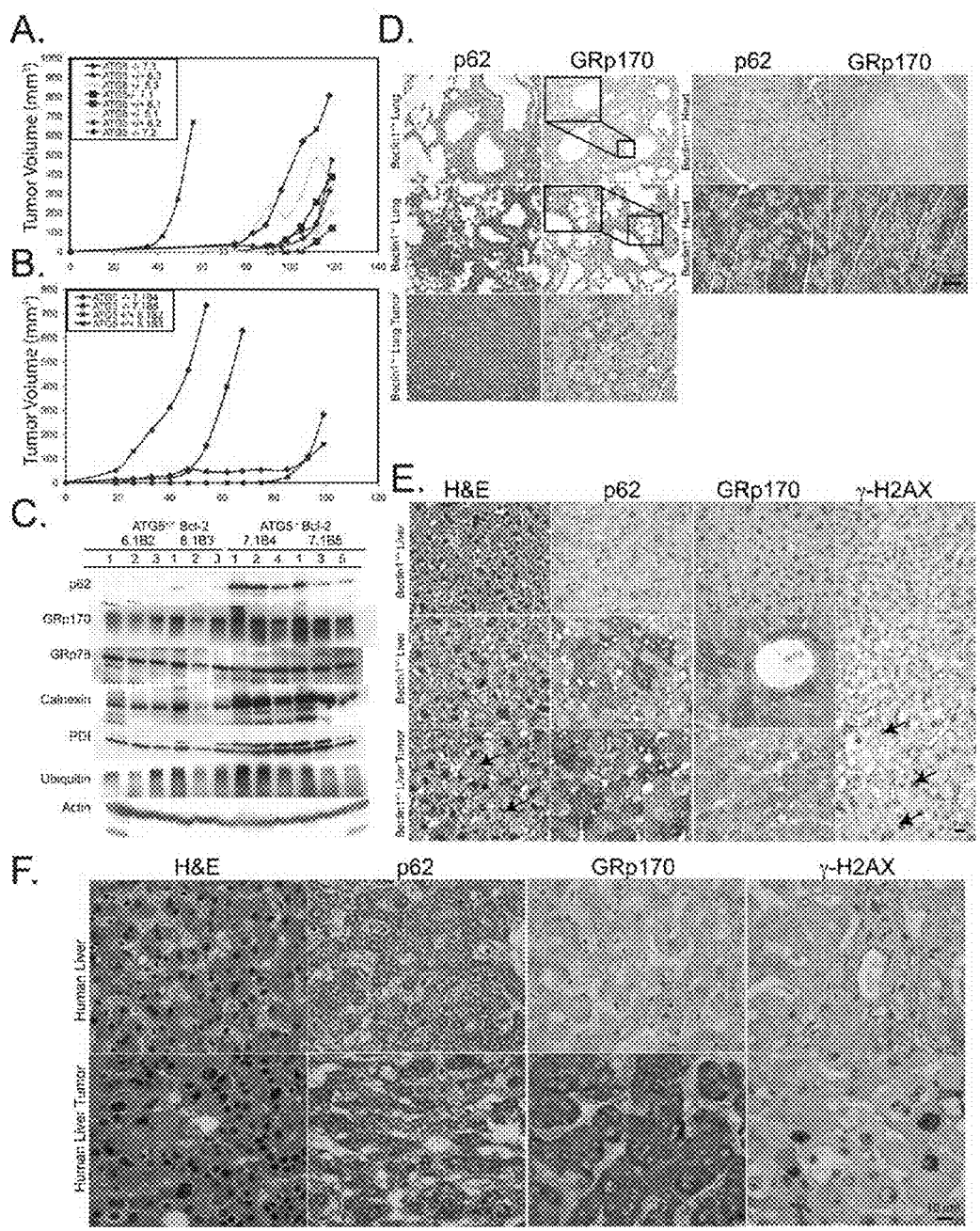
FIG. 4 illustrates elevated ER stress and DNA damage response in autophagy-defective tumors. (A) Deficiency in atg5 in iBMK cells promotes tumorigenesis. Tumor allograft growth of atg5$^{+/+}$ (red)), atg5$^{+/-}$ (yellow) and atg5$^{-/-}$ (blue) iBMK cell lines in nude mice. (B) Deficiency in atg5 cooperates with defective apoptosis enhances tumor growth. Tumor allograft growth of Bcl-2 expressing atg5$^{+/+}$ (red), and atg5$^{-/-}$ (blue) iBMK cell lines in nude mice. (C) Western blot showing elevated levels of p62 and ER chaperones and PDI in Bcl-2 expressing atg5$^{+/+}$ and atg5$^{-/-}$ BMK tumors in (B). (D) Elevated p62 and GRp170 levels in lung and heart tissues and spontaneous lung tumors from beclin1$^{+/-}$ mice. Lung, heart and spontaneous lung tumor sections from two 1.5-year-old beclin1$^{+/+}$ and four 1.5-year-old beclin1$^{+/-}$ mice were stained for p62 and GRp170 by IHC. Stained sections were independently scored and analyzed by Students t-test (lung) or Mann-Whitney test (heart). $p<0.05$ was considered statistically significant. (E) Elevated p62 and GRp170 in liver tissue and p62, Mallory-Denk bodies (H&E, arrows) and γ-H2AX (arrows) in spontaneous liver tumors from beclin1$^{+/-}$ mice (1.5 years). Stained sections were independently scored and analyzed by Students t-test for significance ($p<0.05$). (F) Elevated p62, GRp170, and γ-H2AX positive nuclei in human hepatocellular carcinomas (HCC). Representative images from a human liver TMA (46 samples) showing H&E, p62, GRp170 and γ-H2AX accumulation in HCCs. Corresponding images from a normal human liver TMA (14 samples) are shown for comparison. Stained sections were independently scored and analyzed by Students t-test for significance for significance ($p<0.05$).

Unlike that seen in mouse brain tissue, there is no striking accumulation of polyubiquitinated proteins in tumor cells with defective autophagy, suggesting that there may be tissue-specific differences in autophagy-mediated protein elimination (FIG. 4C). Dilution of polyubiquitinated proteins through active cell division in tumor cells may prevent their accumulation, which is not possible in post-mitotic neurons. Alternatively, proteasome-mediated turnover of polyubiquitinated proteins may be elevated in tumor cells in comparison to neuronal tissues. Indeed, autophagy defects sensitize cancer cells to proteasome inhibitors, suggesting a compensatory function of the two protein degradation pathways.

The persistence of p62 and p62-containing protein aggregates in beclin1 and atg5 mutant cells and tumors indicated a profound defect in the management of protein turnover supported by the associated accumulation of ER chaperones and the oxidative protein folding machinery. This suggested that the inability to degrade damaged or misfolded proteins through autophagy in stressed cells increased the burden on the ER chaperones and oxidative protein folding machinery, necessitating their upregulation. Both p62 and GRp170 were dramatically upregulated in beclin1$^{+/-}$ tissues as well as in spontaneous tumors, indicating that coping with unfolded proteins may be a biomarker for impaired autophagy that precedes tumor initiation.

ER chaperone and PDI upregulation is common in human tumors, and increased GRp170 expression is associated with poor prognosis in breast cancer. Chaperones are stress-responsive and provide a protective function by suppressing the accumulation of unfolded proteins that may be a particularly important compensatory mechanism for autophagy-defective cells. It is important to note that an increased demand for protein folding can be a source of oxidative stress, particularly when cells are overburdened with damaged and unfolded proteins, in concordance with increased ROS in stressed beclin1$^{+/-}$ cells. Interestingly, metabolic stress induces HIF-1α in vitro and in tumors in vivo, and many of the proteins that are induced by metabolic stress and preferentially elevated in autophagy-deficient cells are targets of HIF-1α. While HIF-1α induction promotes autophagy, this may play a role as a negative feedback loop to curtail HIF-1α activation.

Autophagy-defective tumor cells subjected to stress display accumulation of damaged mitochondria as an additional source of oxidative stress. Thus, the accumulation of unfolded protein and protein aggregates and the persistence of damaged mitochondria may collectively lead to elevated ROS production in stressed, autophagy-defective cells. As ROS scavengers partially suppress p62 accumulation and cell death in stressed beclin1$^{+/-}$ tumor cells, this suggests that the elevated oxidative stress contributes to cell damage and death.

Figure 7:
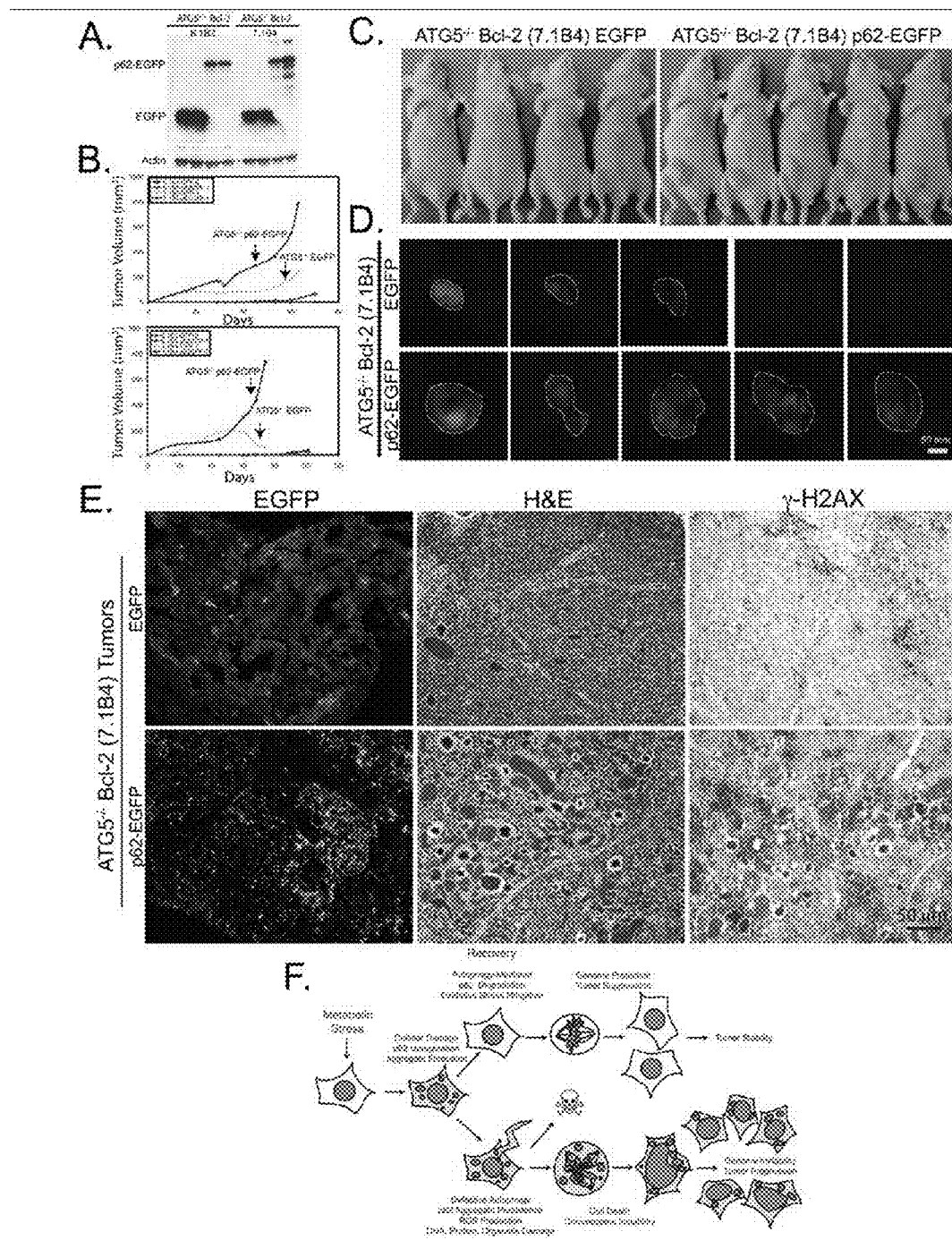
FIG. 7 illustrates how p62 expression cooperates with autophagy-deficiency to promote tumor growth. (A) Western blot for EGFP, in Bcl-2 expressing atg5$^{+/+}$ and atg5$^{-/-}$ iBMK cells stably expressing EGFP or p62-EGFP. (B) Tumor growth of cell lines in (A) showing enhanced tumor growth in p62-EGFP expressing atg5$^{-/-}$ tumors (red) compared to that of the control vector (yellow). (C) Panel showing tumor-bearing mice injected with p62-EGFP-(right panel), and EGFP-expressing (left panel) atg5$^{-/-}$ iBMK cells from (B), at day 74 post-injection. (D) EGFP fluorescence images of individual tumors from EGFP- and p62-EGFP-expressing atg5$^{-/-}$ tumors. (E) Tumors from p62-EGFP expressing atg5$^{-/-}$ cells are associated with p62 aggregates and prevalent polymorphic and γ-H2AX positive nuclei. Representative photomicrographs of frozen tumor sections (left), and paraffin embedded sections stained by H&E (middle) or IHC for γ-H2AX (right) in tumors from atg5$^{-/-}$ cells shown in (C) and (D). (F) A model for the role of autophagy as a tumor suppressor mechanism by limiting p62 accumulation.

Stress-mediated p62 protein accumulation in autophagy-defective cells is sufficient for ROS and DNA damage response induction, whereas wild-type cells eliminated p62 and does not induce ROS or the DNA damage in response to stress. The ability to rescue γ-H2AX-positive nuclear staining in stressed, autophagy-defective cells with knockdown of p62 indicates that this elevated activation of the DNA damage response was attributable directly to p62 accumulation. Thus, the inability of autophagy-defective tumor cells to eliminate p62 contributes to oxidative stress and likely to DNA damage. These observations are strikingly similar to the rescue of oxidative stress toxicity caused by atg7 deficiency with p62 deficiency in mouse liver (Komatsu, M., et al. (2007), Homeostatic Levels of p62 Control Cytoplasmic Inclusion Body Formation in Autophagy-Deficient Mice, *Cell* 131, 1149-1163). In normal tissues, toxicity due to p62 accumulation resulting from autophagy defect may appropriately trigger cell death, whereas in checkpoint-defective tumor cells this instead may result in enhancement of genome instability, mutations and tumor progression.

atg5$^{-/-}$ tumors display pronounced p62 and p62 aggregate accumulation and this p62 expression is sufficient for a remarkable enhancement of tumor growth. Moreover, p62-EGFP but not EGFP-expressing atg5$^{-/-}$ tumors display prevalent polyploid and aneuploid nuclei and are positive for γ-H2AX, indicative of DNA double strand breaks. This indicates that p62 persistence in autophagy-defective cells is sufficient for induction of DNA damage and genome instability associated with enhanced tumor growth. p62 expression, p62 aggregates, and Mallory-Denk bodies that are composed of p62 and other proteins are common in steasosis and in hepatocellular carcinomas and other cancers. Defects in autophagy may be a major mechanism for sustained p62 accumulation and formation of Mallory-Denk bodies. Importantly, it has been shown now that p62 accumulation is not merely a histologic marker for certain cancers, but rather, directly contributes to tumor growth. Examination of a human liver cancer TMA reveals the high frequency of p62, GRp170 and γ-H2AX positive cells similar to what was observed in the autophagy-defective tumor allografts and spontaneous liver tumors arising in beclin1$^{+/-}$ mice. Thus autophagy defects, p62 and ER chaperone accumulation, and DNA damage are common, associated tumor phenotypes. Interestingly, pten, beclin1, or atg7 deficiency produce HCC and liver steatosis in mice, suggesting that constitutive activation of the PI3-kinase pathway and the resulting steatosis may be caused by suppression of autophagy.

p62 normally functions as an adaptor protein by binding to TRAF6 in cell surface receptor signaling complexes that regulate the activation of NF-κB. This function of p62 is also required for efficient oncogene activation in vitro and p62 deficiency suppresses spontaneous lung tumorigenesis by K-ras. Thus, p62 had been identified as an oncoprotein in both loss- and gain-of-function situations (FIG. 7). Alternatively, liver-specific autophagy defects produce p62 accumulation that causes oxidative stress and activation of Nrf2. Thus, the tumor suppressor function of autophagy may be related to the modulation of oxidative stress, Nrf2 or possibly also HIF-1α, and NF-κB pathways. While not intending to be bound by any theory or theories of operation, it is believed that defects in autophagy promote a failure of protein and organelle quality control in tumors that leads to oxidative stress, genome damage and tumorigenesis caused by the inability to eliminate p62 following stress. As p62 upregulation is common in liver tissues of individuals at risk and hepatocellular carcinomas in patients, this suggests that facilitating the clearance of p62 by promoting autophagy may be a strategy for cancer chemoprevention.

Allelic loss of the essential autophagy gene beclin1 occurs in human cancers and renders mice tumor-prone, suggesting that autophagy is a tumor-suppression mechanism. While tumor cells utilize autophagy to survive metabolic stress, autophagy mitigates the resulting genome damage, thus functioning to limit tumorigenesis. In response to stress, autophagy-defective tumor cells preferentially accumulate p62/SQSTM1 (p62) protein aggregates, endoplasmic reticulum (ER) chaperones, damaged mitochondria, reactive oxygen species (ROS), and genome damage. Thus, autophagy may suppress oxidative stress and protein, organelle and DNA damage. Suppressing ROS or p62 accumulation provided protection from damage resulting from autophagy defects. Moreover, stress-mediated p62 accumulation caused by defective autophagy stimulates ROS and the DNA damage response and promotes tumorigenesis. These findings suggest that the tumor-suppressive function of autophagy is related to the prevention of sustained p62 accumulation, oxidative damage and genome instability that enable tumor progression. While not intending to be limited by any theory or theories of operation, defective autophagy is believed to be a mechanism for p62 upregulation commonly observed in human tumors that contributes directly to tumorigenesis.

Stimulating autophagy may be critically important to limit the progression of certain diseases, including, but not limited to, neurodegeneration, liver disease, and also cancer, by facilitating the elimination of protein aggregates, damaged organelles, and the toxic consequences of their accumulation. In individuals at risk for hepatocellular carcinoma (HCC), autophagy stimulators may be particularly indicated to limit liver damage and disease progression for cancer chemoprevention. Thus, the autophagy pathway provides a basis for novel therapeutic target identification for drug discovery for many diseases with respect to both acute treatment and also disease prevention.

Figure 12:
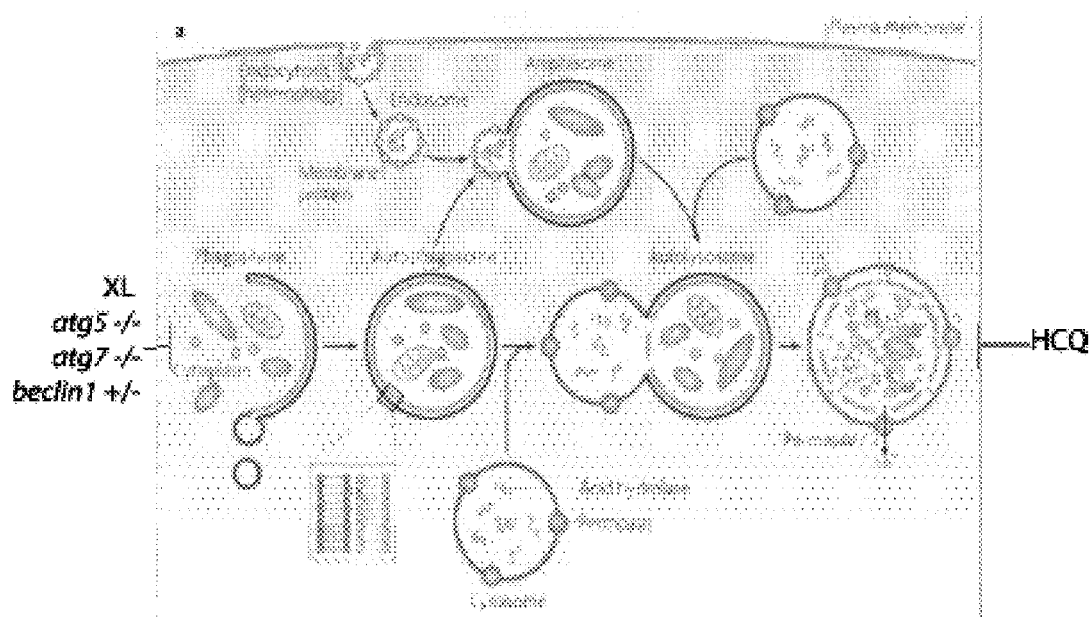
FIG. 12 illustrates an overview of the autophagic pathway and points of inhibition. Abbreviations: XL (Exelixis Vps34 inhibitors), HCQ (hydroxychloroquine)

Identification of the therapeutic means to inhibit the autophagy survival pathway in tumor cells would be advantageous. This may be especially important as many therapeutics currently in use, such as kinase and angiogenesis inhibitors, inflict metabolic stress, which increases the dependency on autophagy for survival. Furthermore, tumor cells with impaired autophagy are particularly vulnerable to metabolic stress and further therapeutic suppression of autophagy may exploit this vulnerability by promoting cell death by metabolic catastrophe or the failure to mitigate cell damage accumulation. In support of these hypotheses, preclinical findings using hydroxychloroquine (HCQ) to inhibit lysosome acidification and thereby autophagy in combination therapy have been described (FIG. 12). Specific inhibitors of the autophagy survival pathway in tumor cells, including, without limitation, Vps34 inhibitors (available from Exelixis), may be used in combination with agents such as for example, angiogenesis and kinase inhibitors that promote metabolic stress (FIG. 12). In contrast to most currently available therapies that target proliferating tumor cells, autophagy inhibition may be used to target nondividing and potentially even dormant tumor cells.

To address the need for the identification of autophagy inhibitors for cancer prevention and/or treatment and autophagy stimulators for the prevention and treatment of disease, cell-based screens are described. Specific embodiments include shRNA screens as well as small molecule screens.

In certain embodiments, a small hairpin RNA (shRNA) screen may be used. shRNA screens may utilize, without limitation, kinase, phosphatase, and/or metabolism shRNA lentivirus library subsets. In certain embodiments, lentivirus libraries may include approximately 5000 genes in triplicate. Lentiviruses are high-titer, individual clones with representation of five independent hairpins for each target gene supplied in a high-throughput format (Root, D. E., Hacohen, N., Hahn, W. C., Lander, E. S., and Sabatini, D. M. (2006), Genome-scale loss-of-function screening with a lentiviral RNAi library, *Nature Methods* 3, 715-719.).

In other embodiments of the invention, small molecule screens may be used. Such assays may utilize chemical libraries. Useful libraries include, but are not limited to, the National Cancer Institute (NCI) training set, Diversity set, Maybridge, and the Main library. Fluorescence image analysis may be used to capture the data. Positive clones may be subject to subsequent independent verification.

According to certain embodiments, useful cell lines for the screens include genetically defined immortal mouse epithelial cell lines derived from wild type or autophagy deficient mice with well-characterized phenotypes in vitro and in vivo (Degenhardt et al., 2006; Mathew et al., 2007b; Karantza-Wadsworth et al., 2007). In preferred embodiments, useful cell lines that may be employed in the described screens include cells having the phenotype(s) including, but not limited to, beclin1$^{+/-}$, atg5$^{-/-}$, and/or atg7$^{-/-}$. Cell may be derived from multiple tissues. Preferably, the cell lines are derived from mouse tissues. In certain preferred embodiments, the cell line comprises immortalized baby mouse kidney epithelial cells.

Genes and compounds identified in the screens may be validated in vitro and/or in vivo. Tissues and spontaneous tumors from mouse models may be collected for validation purposes. Conditional knockouts may also be used for validation.

EXAMPLES

The following examples serve to more fully describe the manner of using the above-described invention. It is understood that these examples in no way serve to limit the true scope of this invention, but rather are presented for illustrative purposes.

Materials and Methods

Generation of Stable Cell Lines and Culture Conditions

Primary epithelial cells from atg5$^{+/+}$, atg5$^{+/-}$, atg5$^{-/-}$, beclin1$^{+/+}$ and beclin1$^{+/-}$ mice were immortalized to generate iBMK cell lines (Degenhardt, K., et al. (2006), Autophagy promotes tumor cell survival and restricts necrosis, inflammation, and tumorigenesis, *Cancer Cell* 10, 51-64; Degenhardt, K., et al., (2002) Bax and Bak independently promote cytochrome C release from mitochondria, *J Biol Chem* 277, 14127-14134; Mathew, R., Degenhardt, K., Haramaty, L., Karp, C. M., and White, E. (2008), Immortalized mouse epithelial cell models to study the role of apoptosis in cancer, *Methods Enzymol*, 446, 77-106; Mathew, R., Kongara, S., Beaudoin, B., Karp, C. M., Bray, K., Degenhardt, K., Chen, G., Jin, S., and White, E. (2007b), Autophagy suppresses tumor progression by limiting chromosomal instability, *Genes Dev* 21, 1367-1381). Bcl-2 expressing atg5$^{+/+}$ and atg5$^{-/-}$ iBMK cells were engineered to stably express myc-tagged p62 (pcDNA3-myc-p62), EGFP (pEGFPC1) or p62-EGFP (pEGFPC1-p62) (Rodriguez, A., et al. (2006), Mature-onset obesity and insulin resistance in mice deficient in the signaling adapter p62, *Cell Metab* 3, 211-222), co-transfected with pcDNA3-Zeo by electroporation (Nelson, D. A., et al. (2004) Hypoxia and defective apoptosis drive genomic instability and tumorigenesis, *Genes Dev* 18, 2095-2107). Independent clones were selected in zeocin (500 µg/mL) and expanded as stable cell lines in normal culture conditions (DMEM, 10% FBS, 1% Pen Strep (Invitrogen, Carlsbad, Calif.) at 38.5° C. and 8.5% $CO_2$) (Mathew, R., Degenhardt, K., Haramaty, L., Karp, C. M., and White, E. (2008)). To induce metabolic stress, cells were placed in glucose-free DMEM (Invitrogen) containing 10% FBS and incubated with a defined gas mixture containing 1% oxygen, 5% $CO_2$ and 94% $N_2$ (GTS-Welco, Allentown, Pa.) (Nelson et al., 2004). NAC (Sigma-Aldrich, St. Louis, Mo.) was used at a concentration of 1 mM.

Example 1

Autophagy-Defective Tumor Cells Accumulate p62 in Response to Stress

To address the potential role of autophagy-dependant protein quality control in tumor suppression, p62 modulation was assessed during metabolic stress and recovery in autophagy-competent (beclin1$^{+/+}$ and atg5$^{+/+}$) and autophagy-defective (beclin1$^{+/-}$ and atg5$^{-/-}$) immortalized baby mouse kidney (iBMK) cells. Cells were engineered to express Bcl-2, as the assessment of autophagy is facilitated in an apoptosis-defective background (Degenhardt, K., et al. (2006), Autophagy promotes tumor cell survival and restricts necrosis, inflammation, and tumorigenesis, *Cancer Cell* 10, 51-64; Lum, J. J., et al., (2005), Growth factor regulation of autophagy and cell survival in the absence of apoptosis, *Cell* 120, 237-248). Under normal growth conditions, p62 levels were low in wild-type cells and slightly elevated in autophagy-defective iBMK cells (FIG. 1B). Following 7 days of metabolic stress there was dramatic p62 induction in wild-type cells that was further elevated in autophagy-defective cells in a predominantly punctate pattern suggestive of p62 aggregation. In wild-type cells, most p62 aggregates were eliminated within 24 hr of recovery, whereas p62 remained predominantly in large aggregates in autophagy-defective cells (FIG. 1B). p62 aggregates persisted in mutant cells after 2 days of recovery (FIG. 1B) and remained so for at least a week (data not shown), indicating that autophagy is required to limit the formation and to promote the clearance of p62. Consistent with this, higher p62 levels were observed in autophagy-deficient (atg5$^{-/-}$), as compared to wild-type (atg5$^{+/+}$) iBMK cells stably expressing myc-tagged p62 (myc-p62) (FIG. 1C). Thus, metabolic stress induced p62 accumulation and aggregate formation, requiring autophagy for elimination.

Example 2

Figure 2:
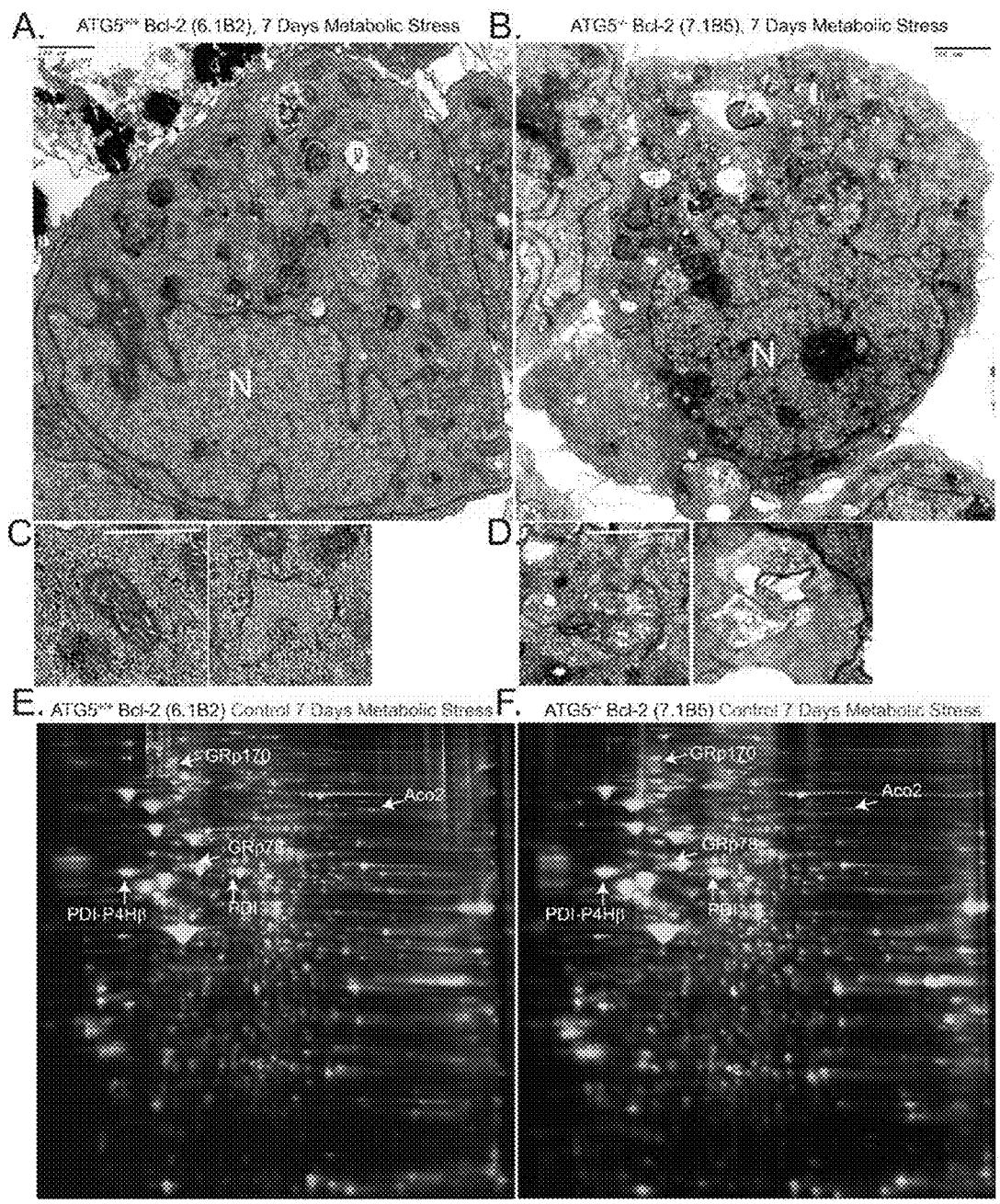
FIG. 2 illustrates effects of metabolic stress in promoting organelle damage and ER chaperones and PDI upregulation in autophagy-deficient cells. (A-D) Representative electron micrographs of Bcl-2 expressing atg5$^{+/+}$ (A) or atg5$^{-/-}$ (B) cells following 7 days of metabolic stress. A wild-type cell (A) showing mitochondria (M, blue arrows and C, left panel), ER (E, red arrows and C, right panel), mutant cell in (B) showing mitochondria (M, blue arrows and D, left panel), and protein aggregates (A, yellow and D, right panel). (E and F) 2-DIGE gels showing differential regulation of ER chaperones (GRp170, GRp78), PDI, PDI-P4Hβ and ACO2 in Bcl-2 expressing atg5$^{-/-}$ iBMK cells in response to metabolic stress (7 days). Total protein from unstressed or metabolically stressed (7 days) Bcl-2 expressing atg5$^{+/+}$ and atg5$^{-/-}$ cell lines were labeled with Cy3 (Green-unstressed) or Cy5 (Red-stressed) and analyzed by 2-DIGE. Images show 2-DIGE gels with proteins that are induced (Red), repressed (Green) or unchanged (Yellow) under metabolic stress. Protein spots (n=106) that were differentially induced were selected and identified by mass spectrometry.

Autophagy-Defective Tumor Cells Accumulate Damaged Mitochondria ER Chaperones and PDIs Apoptosis-deficient atg5$^{+/+}$ iBMK cells responded to prolonged stress by undergoing progressive autophagy, yielding cells less than one-third their original size that retained numerous well-preserved mitochondria (M), and ER appeared slightly distended (E) indicative of an unfolded protein response (UPR) (FIGS. 2A and 2C). In contrast, Bcl-2-expressing atg5$^{-/-}$ (FIG. 2B) and beclin1$^{+/-}$ (data not shown) iBMK cells showed disintegrating mitochondria with gross structural abnormalities (M) and large, abnormal cytoplasmic structures (A) resembling protein aggregates (FIGS. 2B and 2D), consistent with p62 aggregate accumulation (FIG. 1B). Thus, autophagy may function to prevent the accumulation of protein aggregates and damaged organelles during metabolic stress.

Since tumor cells with defective autophagy displayed failure of protein quality control, two-dimensional difference in gel electrophoresis (2-DIGE) coupled with mass spectrometry were performed to characterize the impact on the cellular proteome. Autophagy-competent, apoptosis-defective (bax$^{-/-}$/bak$^{-/-}$) D3 iBMK cells manage long-term metabolic stress by activation of autophagy. In response to metabolic stress, D3 cells induced ER chaperones (GRp170, GRp78, calreticulin), PDIs metabolism and mitochondrial proteins (FIGS. 2C and 2D). Some of these proteins (triosphosphate isomerase-1 [TPI-1]; phosphoglycerate kinase 1 [PGK-1]; pyruvate kinase 3 [PK-3]; glycerol-3-phosphate dehydrogenase [GPDH]) are targets of hypoxia inducible factor-1 cc (HIF-1α) indicative of metabolic adaptation, and HIF-1α is induced in iBMK cells by metabolic stress in vitro and in tumors in vivo. Similarly to D3 cells under metabolic stress proteomic analysis of Bcl-2 expressing autophagy-competent beclin1$^{+/+}$ and atg5$^{+/+}$ iBMK cells induced ER chaperones GRp170, GRp78, calreticulin and calnexin indicating that metabolic stress response was not influenced by the means of apoptosis inactivation. To determine if autophagy-deficiency altered this stress response, Bcl-2 expressing, apoptosis and autophagy-defective (beclin1$^{+/-}$ and atg5$^{-/-}$) iBMK cells were examined by 2-DIGE in parallel. Autophagy-defective cells displayed preferential upregulation of ER chaperones compared to the wild-type cells (FIGS. 2E and 2F). Allelic loss of beclin1 was associated with marked differential increase in GRp170, GRp78, calreticulin and calnexin while atg5$^{-/-}$ cells showed differential increase in GRp170, GRp78 and calnexin compared to the wild-type cells. For example, GRp170 levels were induced by 3- to almost 9-fold in autophagy-competent (D3, beclin1$^{+/+}$ and atg5$^{+/+}$) cells whereas induction was more than 8-fold in autophagy-deficient (beclin1$^{+/-}$ and atg5$^{-/-}$) cells under metabolic stress (FIG. 2F). A similar but less striking differential increase was also observed in GRp78 levels in beclin1$^{+/-}$ and atg5$^{-/-}$ cells. Members of the PDI family of proteins such as PDI and PDI-prolyl 4-hydroxylase-β subunit (PDI-P4Hβ) instrumental in refolding misfolded proteins in the ER lumen, were induced under metabolic stress and were further elevated by autophagy-deficiency (FIGS. 2E and 2F). It is hypothesized that the lack of induction of calreticulin and PDI-P4Hβ by metabolic stress in atg5$^{-/-}$ iBMK cells, may be due to their increased susceptibility to metabolic stress. Interestingly, levels of cytoskeletal and protein synthesis-related proteins were repressed with stress in all cell lines. This differential induction of ER chaperones and oxidative protein folding machinery in the autophagy-deficient cells under stress suggests a role for autophagy in mitigating ER stress by eliminating unfolded proteins through lysosomal degradation.

Figure 3:
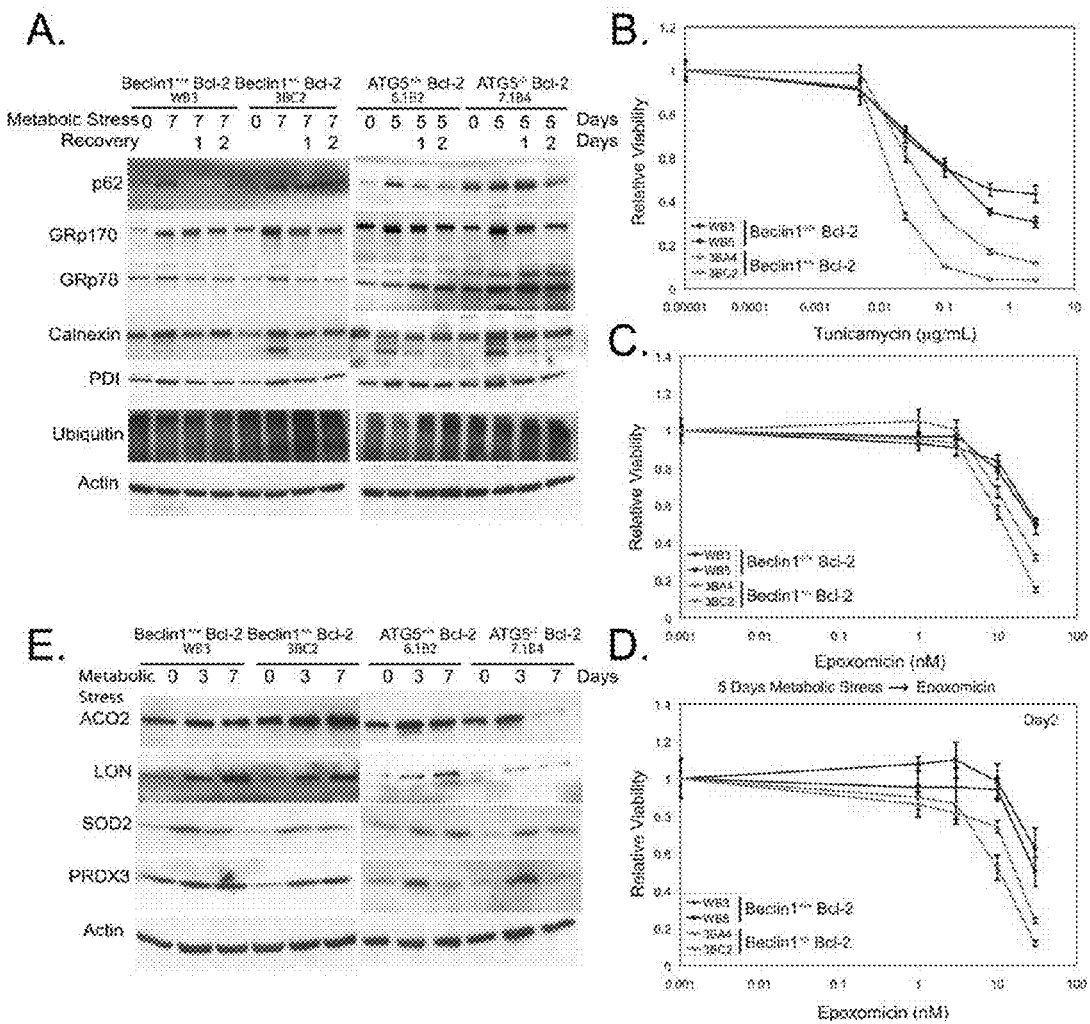
FIG. 3 illustrates the effects of autophagy defects in altering the stress response and sensitize cells to ER stress and proteasome inhibition. (A) Western blots showing levels of p62, ER chaperones, PDI and ubiquitin in Bcl-2 expressing beclin1$^{+/+}$, beclin1$^{+/-}$, atg5$^{+/+}$ and atg5$^{-/-}$ iBMK cells following 5 or 7 days of metabolic stress, and 1 and 2 days of recovery. (B-D) Allelic loss of beclin1 sensitizes cells selectively to ER stress and proteasome inhibition. MTT assays showing sensitivity of Bcl-2 expressing beclin1$^{+/+}$ (Blue) and beclin1$^{+/-}$ (Red) iBMK cells in response to increasing concentrations of (B) tunicamycin for 3 days, or (C) epoxomycin for 2 days, and (D) following 5 days of metabolic stress. Data are presented as mean±SD. (E) Autophagy deficiency causes mitochondrial damage. Western blots showing levels of mitochondrial proteins (ACO2, LON, SOD2 and PRDX3) in Bcl-2 expressing beclin1$^{+/+}$, beclin1$^{+/-}$, atg5$^{+/+}$ and atg5$^{-/-}$ iBMK cells, following 0, 3 and 7 days of metabolic stress.

Individual proteins and their degradation fragments can be represented by multiple spots in 2-DIGE and this complicates estimation of protein levels by spot volume ratios. Thus, ER chaperones identified as differentially regulated by 2-DIGE were further examined by Western blotting. p62 and ER chaperones GRp170, GRp78, calnexin and PDI, and showed higher induction in beclin1$^{+/-}$ and atg5$^{-/-}$ compared to beclin1$^{+/+}$ and atg5$^{+/+}$ cells under stress (FIG. 3A) consistent with p62 immunofluorescence (IF) (FIG. 1B) and proteomic analysis. As with p62 aggregates, elevated and persistent levels of these proteins were more evident in atg5$^{-/-}$ and beclin1$^{+/-}$ cells during 1-2 days of recovery from metabolic stress (FIG. 3A). Together, these results suggested that autophagy defects accentuated the demand for protein folding under metabolic stress that persists during recovery.

Example 3

Autophagy Defects Cause Sensitivity to ER Stress

Since autophagy defects indicated an elevated demand for protein folding, the sensitivity of beclin1 cells to pharmacological induction of ER stress was investigated. Tunicamycin induces ER stress by inhibiting protein glycosylation and allelic loss of beclin1 caused increased sensitivity to this drug when compared to wild-type cells (FIG. 3B). Degradation of unfolded proteins via the proteasome pathway and ameliorates ER stress and to investigate if autophagy deficiency also elevated the burden on the ubiquitin-proteasome system, the sensitivity to the proteasome inhibitor epoxomycin was assessed. Autophagy-defective cells displayed increased sensitivity to proteasome inhibition, which was further exacerbated by metabolic stress (FIGS. 3C and 3D). This suggests an increased dependency of autophagy-defective cells on proteasome pathway particularly during metabolic stress. Thus, autophagy may function to maintain protein quality control cooperatively with the ubiquitin-proteasome pathway, consistent with the observation that suppression of proteasome function activates autophagy, the inhibition of which promotes cell death (Ding, W. X., et al., (2007), Linking of autophagy to ubiquitin-proteasome system is important for the regulation of endoplasmic reticulum stress and cell viability, *Am J Pathol* 171, 513-524).

EM revealed preferential accumulation of morphologically abnormal mitochondria in autophagy-deficient cells (FIGS. 2A-2D) and stressed atg5$^{-/-}$ cells showed aberrant regulation of mitochondrial proteins such as aconitase (ACO2) (FIGS. 2E and 2F) consistent with mitochondrial deterioration. ACO2 is a mitochondrial ROS sensor that responds to, and accumulates under, mitochondrial oxidative stress whereupon it either aggregates or is degraded by its specific protease LON. Consistent with the profound induction of stress proteins and mitochondrial damage, autophagy-deficient cells showed markedly increased (beclin1$^{+/-}$) or reduced (atg5$^{-/-}$) levels of ACO2 after 7 days of metabolic stress compared to the wild-type cells (FIG. 3E). Furthermore, LON, which is responsible for the degradation of the oxidized form of ACO2, showed progressively increasing levels under metabolic stress, as was also observed for oxidative stress markers such as superoxide dismutase (SOD2) and peroxiredoxin (PRDX3) that were not sustained in autophagy-defective cells (FIG. 3E). These results suggested that autophagy defects are associated with mitochondrial deterioration under metabolic stress.

Example 4

Defects in Autophagy Cause Upregulation of p62 and ER Chaperones in Tumors

To assess whether the differential accumulation of p62, ER chaperones and PDI was also a feature of autophagy defects in tumors, Bcl-2 expressing atg5$^{+/+}$ and atg5$^{-/-}$, and beclin1$^{+/+}$ and beclin1$^{+/-}$ iBMK tumor allografts, and spontaneous tumors from beclin1$^{+/-}$ mice were examined. As with autophagy defects caused by allelic loss of beclin1 in iBMK cells, deficiency in atg5 increased tumorigenesis and cooperated with defects in apoptosis to accelerate tumor growth (FIG. 4B). All Bcl-2 expressing atg5$^{-/-}$ tumors displayed elevated p62, GRp170, GRp78, calnexin, and PDI compared to the wild-type by Western blotting (FIG. 4C) as did Bcl-2 expressing beclin1$^{+/-}$ and atg5$^{-/-}$ tumors by immunohistochemistry (IHC) (data not shown). Upregulation of ubiquitinated proteins, although common in tissues of autophagy-defective mice was less striking in atg5$^{-/-}$ tumors (FIG. 4C) and may reflect the rapidly dividing state of these cells. Additionally, histological analyses of tissues (lung, heart, and liver) and spontaneous lung and liver tumors from 1.5 year-old beclin1$^{+/-}$ mice showed significant accumulation of p62 (lung, p<0.029, t-test; heart, p<0.025, Mann-Whitney test) and GRp170 (lung, p<0.0001, t-test; heart, p<0.028, Mann-Whitney test) when compared with age-matched tissues from beclin1$^{+/+}$ littermates (FIGS. 4D and 4E). This suggested that failure of autophagy-mediated protein degradation due to allelic loss of beclin1 in vivo caused elevated ER chaperone levels as a compensation mechanism when proteins destined for degradation were not eliminated through autophagy and that this phenotype is manifested in tissues and spontaneous tumors.

p62 and ER chaperone upregulation are common in human tumors and are often associated with poor prognosis. Human hepatocellular carcinoma (HCC) in particular, is associated with dramatic p62 accumulation in Mallory-Denk bodies, and beclin1$^{+/-}$ mice display p62 accumulation in liver in association with steatohepatitis and spontaneous liver tumors (FIG. 4E), suggesting that autophagy defects may play a prominent role in HCC etiology. Indeed, liver and spontaneous liver tumors from beclin1$^{+/-}$ mice also showed significantly higher levels of p62 (p<0.002, t-test), GRp170 (p<0.003, t-test) and DNA damage response activation (γ-H2AX positive nuclei) (p<0.014, t-test) compared to the normal liver tissues from age-matched beclin1$^{+/+}$ mice (FIG. 4E). Therefore, p62, GRp170 and the DNA damage response (γ-H2AX) were examined in a panel of human liver and HCCs from a liver tissue microarray (TMA) by IHC. Indeed, p62 (p<0.0001, t-test) and GRp170 (p<0.0001, t-test) were significantly upregulated with high frequency in HCC compared with normal liver (FIG. 4F). Moreover, as with spontaneous liver tumors in beclin1$^{+/-}$ mice (FIG. 4E), human HCCs were also associated with higher levels of γ-H2AX positive nuclei (p<0.03, t-test) compared to normal liver samples (FIG. 4F). These results suggest that, as with stressed autophagy-deficient cells, accumulation of p62 and GRp170 in human tumors may be a common symptom of defective autophagy manifesting as accumulation of unfolded proteins associated with activation of the DNA damage response. Moreover, failure of protein and organelle quality control caused by autophagy defects may cause elevated oxidative stress and DNA damage that may be genotoxic.

Example 5

Autophagy Mitigates Oxidative Stress and Progression to Aneuploidy

Activation of the DNA damage response is a hallmark of oxidative stress that can be elevated due to increased ROS levels. Protein re-folding in the ER by PDIs can enhance oxidative stress through redox reactions involving free radicals. Additionally, the mitochondrial stress and damage frequently observed in autophagy-deficient cells (FIGS. 2 and 3) can be a potential source of ROS. Since autophagy deficiency preferentially causes the accumulation of p62 aggregates, damaged mitochondria and upregulation of oxidative protein folding machinery under metabolic stress and is associated with activation of the DNA damage response in tumors, the ROS levels in beclin1$^{+/+}$ and beclin1$^{-/-}$ cells was examined.

Figure 5:
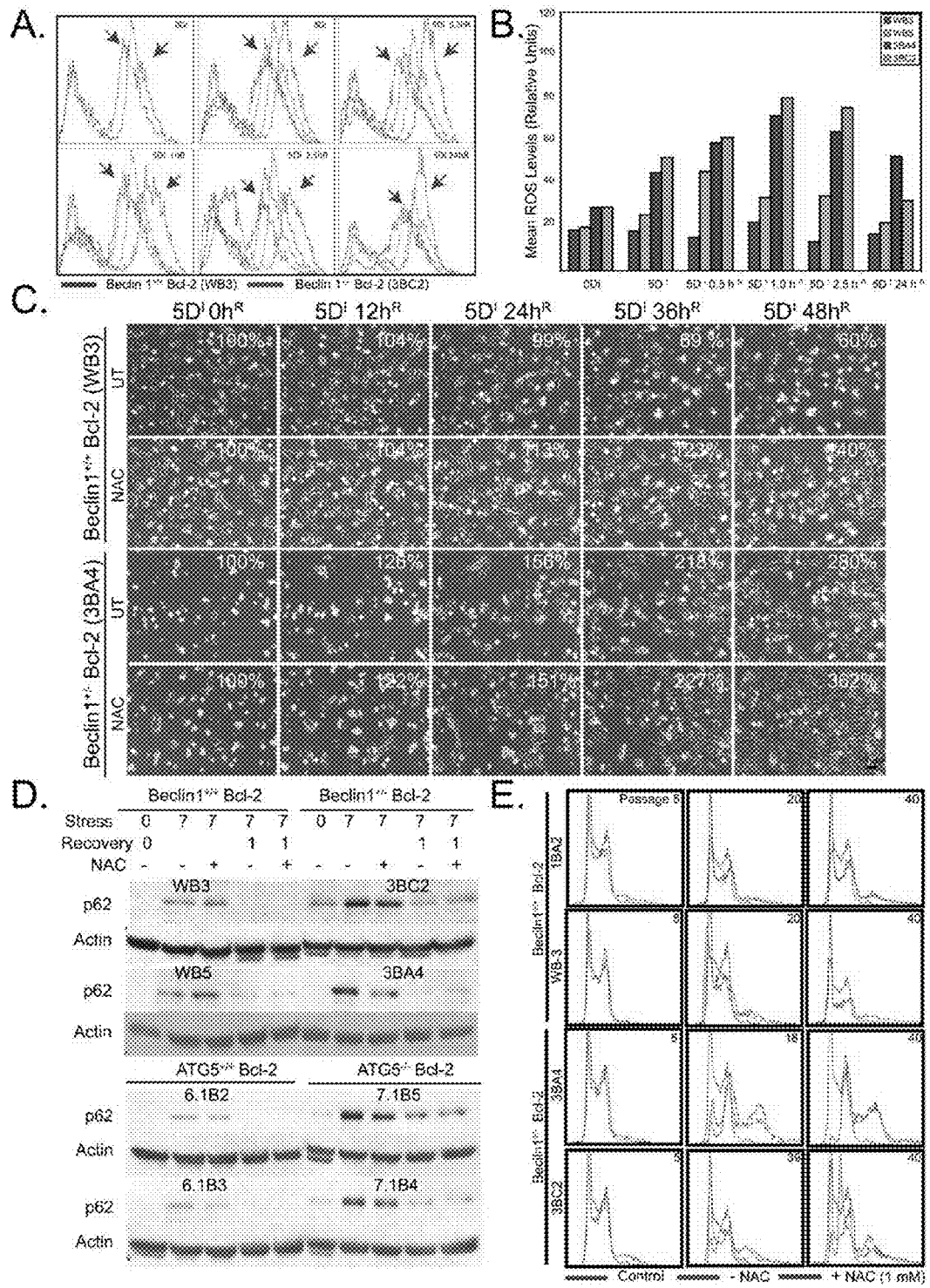
FIG. 5 illustrates effects of metabolic stress in promoting elevated ROS production and chromosomal instability in autophagy-deficient cells. (A) Autophagy-deficiency leads to elevated ROS production. Overlays show ROS levels in Bcl-2 expressing beclin1$^{+/+}$ (Green) and beclin1$^{+/-}$ iBMK cells (Blue) (x-axis, log scale) under normal growth (0 Di) and at 0.5, 1, 2.5 and 24 hr (beclin1$^{+/+}$, green arrows and beclin1$^{+/-}$, red arrows) during recovery (0.5-24 hR) from 5 days of metabolic stress (5 Di) by flow-cytometry using the ROS sensor DCF-DA. The ROS levels in untreated cells are shown in dotted lines for comparison. (B) Representative histogram from three independent experiments measuring the mean ROS levels in Bcl-2 expressing beclin1$^{+/+}$ and beclin1$^{+/-}$ iBMK cells shown in (A). (C) ROS scavenging partially rescues the susceptibility to metabolic stress and recovery due to allelic loss of beclin1. Representative time-lapse images of Bcl-2 expressing beclin1$^{+/+}$ and beclin1$^{+/-}$ iBMK cells during recovery following 5 days of metabolic stress in presence (NAC) and absence (UT) of the ROS scavenger NAC (1 mM) (relative percentage of adherent cells compared to time 0 is shown). (D) ROS scavenging suppresses p62 accumulation in autophagy-deficient (beclin1$^{+/-}$ and atg5$^{-/-}$) cells. Western blot analysis of p62 levels in Bcl-2 expressing beclin1$^{+/+}$, beclin1$^{+/-}$, atg5$^{+/+}$ and atg5$^{-/-}$ iBMK cell lines following 0 or 7 days of metabolic stress followed by 1 day recovery without and with NAC. (E) ROS scavenging limits progression to aneuploidy associated with allelic loss of beclin1. Flow-cytometry analysis of DNA content in diploid, Bcl-2 expressing beclin1$^{+/+}$ and beclin1$^{+/-}$ iBMK cells grown in presence (blue) or absence (red) of the ROS scavenger NAC (1 mM). Numbers represent passage numbers at which ploidy was determined.

Under normal growth conditions ROS levels were slightly elevated in the beclin1$^{+/-}$ iBMK cells compared to the wild-type cells, however, following 5 days of metabolic stress there was a marked increase in beclin1$^{+/-}$ cells (FIGS. 5A and 5B). During recovery, ROS levels either remained unchanged or slightly increased in the beclin1$^{+/+}$ iBMK cells and returned to normal levels by 24 hr whereas, beclin1$^{+/-}$ iBMK showed a marked increase in ROS levels most apparent after 1 hr that persisted following 24 hr of recovery (FIGS. 5A and 5B). These results indicated that allelic loss of beclin1 was associated with elevated and persistent ROS production throughout metabolic stress and recovery.

To determine if the elevated ROS and oxidative stress in autophagy-deficient cells contributes to cellular damage, the stress response without and with the ROS scavenger, N-acetyl cysteine (NAC) was examined. Following 5 days of metabolic stress, Bcl-2 expressing beclin1$^{+/-}$ iBMK cells showed increased susceptibility to stress compared to wild-type cells (FIG. 5C). The presence of NAC during metabolic stress improved survival, and this protective effect was more profound in beclin1$^{+/-}$ cells, suggesting that elevated induction and poor management of ROS levels are partly responsible for the increased susceptibility of autophagy-defective cells to metabolic stress (FIG. 5C). This enhanced survival provided by NAC was associated with decreased p62 accumulation during metabolic stress in the beclin1$^{+/-}$ iBMK cells (FIG. 5D), suggesting that ROS-mediated oxidative stress can lead to protein damage and accumulation of p62 aggregates. A key feature of genomic instability associated with autophagy defects is the accelerated progression to aneuploidy under normal culture conditions. To examine the role of increased ROS levels and oxidative stress on genomic instability, the DNA content of early passage diploid beclin1$^{+/+}$, and autophagy-deficient beclin1$^{+/-}$ iBMK cells without and with NAC by flow-cytometry were monitored. beclin1$^{+/+}$ iBMK cells maintained diploidy after 40 passages and the presence of NAC had no effect. In contrast, beclin1$^{+/-}$ cells showed accelerated progression to aneuploidy by passages 18 and 39 (FIG. 5E), and NAC delayed this progression (FIG. 5E), indicating a causative role for persistent basal ROS-mediated oxidative stress in progression to aneuploidy associated with autophagy defects. Thus, metabolic stress causes p62 accumulation mediated in part by elevated ROS production and the failure to suppress this ROS accumulation in autophagy-deficient cells is associated with genomic instability.

Example 6 p62 Accumulation is Sufficient to Activate the DNA Damage Response

Figure 6:
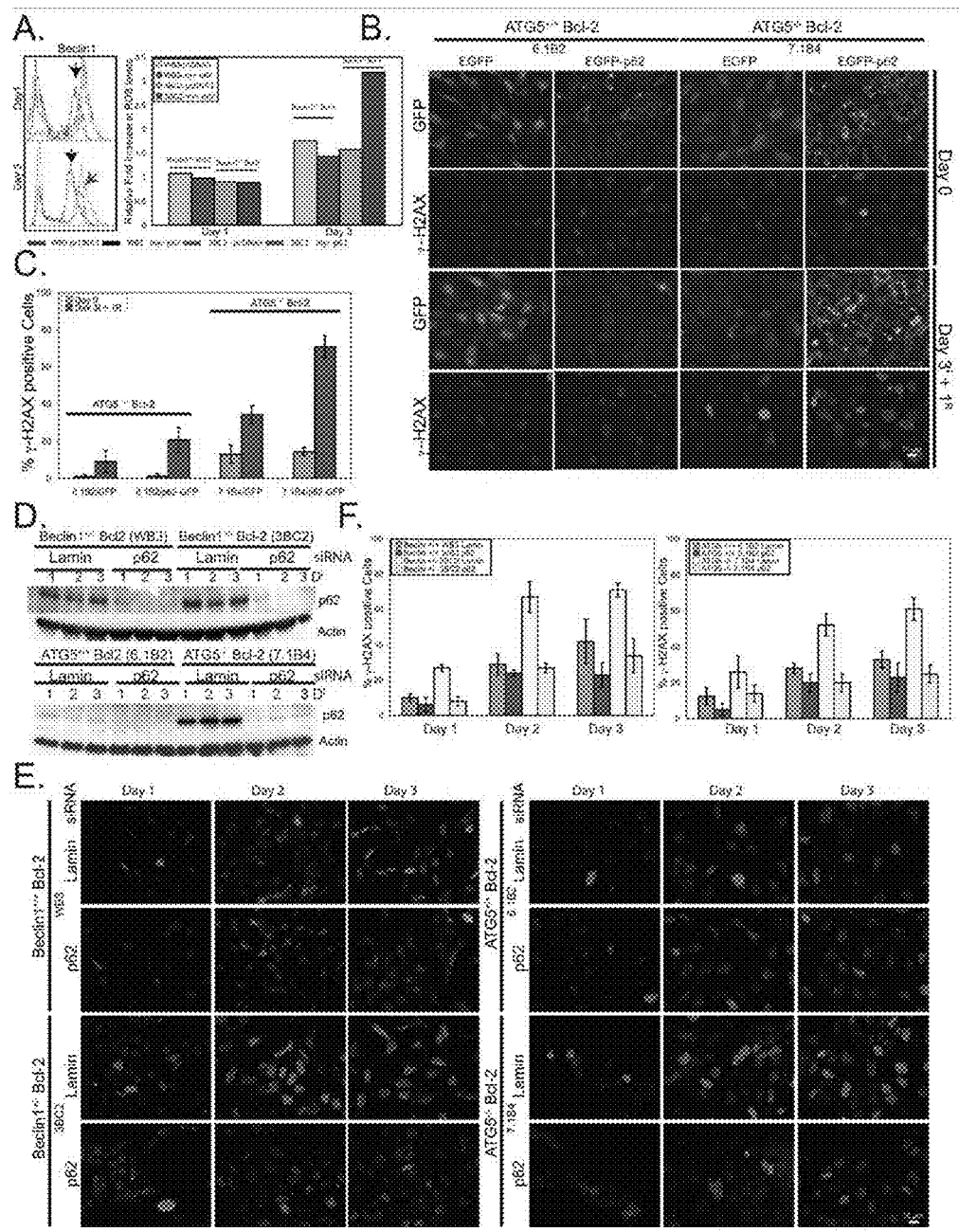
FIG. 6 illustrates the effects of failure to eliminate p62 by autophagy in activating the DNA damage response. (A) p62 expression leads to elevated ROS production in the autophagy-defective beclin1$^{+/-}$ cells. Bcl-2 expressing beclin1$^{+/+}$ and beclin1$^{+/-}$ iBMK cells were transfected with myc-tagged p62 or control vector and ROS levels (DCF-DA) were measured by flow-cytometry at day 3 post-transfection. Histogram on the right is representative of three independent experiments measuring mean ROS level in each cell line on days 1 and 3 post-transfection. (B) Failure to eliminate p62 by autophagy under metabolic stress leads to DNA damage response induction. Bcl-2 expressing atg5$^{+/+}$ or atg5$^{-/-}$ iBMK cells stably expressing EGFP or p62-EGFP were subjected to 3 days of metabolic stress, allowed to recover for 1 day and stained for γ-H2AX. (C) Quantitation of the percentage cells with γ-H2AX positive foci in cells shown in (B), before and during recovery from 3 days of metabolic stress. Data from 200 cells are presented as mean±SD. (D) Western blots showing RNAi-mediated knockdown of p62 levels. Bcl-2 expressing wild-type (beclin1$^{+/+}$ and atg5$^{+/+}$) and autophagy-defective (beclin1$^{+/-}$ and atg5$^{-/-}$) iBMK cells were transfected with either Lamin- or p62-siRNA and subjected to metabolic stress for 0, 24, 48 or 72 hr (24, 48, 72 and 96 hr post-transfection, respectively) and total protein was analyzed for p62 levels. (E) p62 accumulation in autophagy-defective cells is responsible for activation of the DNA damage response. Bcl-2 expressing beclin1$^{+/+}$, beclin1$^{+/-}$, atg5$^{+/+}$ and atg5$^{-/-}$ iBMK cells (D), transfected with either Lamin- or p62-siRNA were subjected to metabolic stress for the indicated time and evaluated for γ-H2AX positive nuclei. (F) Quantitation of percentage cells with γ-H2AX positive nuclei from the data shown in (E). Data from two hundred cells are presented as mean±SD.

Since autophagy deficiency leads to accumulation of p62, oxidative stress and accelerated progression to aneuploidy, it was examined whether accumulation of p62 was sufficient to induce ROS and the DNA damage response. Transient expression of p62-EGFP formed aggregates and was sufficient to elevate ROS levels in the autophagy-deficient (beclin1$^{+/-}$ and atg5$^{-/-}$), but not in the wild-type cells, whereas EGFP expression alone did not induce ROS in either (FIG. 6A). Transient p62-EGFP expression was also associated with DNA damage response activation (γ-H2AX positive nuclei) in autophagy-deficient (beclin1$^{+/-}$ and atg5$^{-/-}$) cells compared to wild-type cells. In order to monitor the accumulation and clearance of p62, apoptosis-deficient atg5$^{+/+}$ and atg5$^{-/-}$ iBMK cells engineered to stably express either EGFP or p62-EGFP were subjected to 3 days of metabolic stress followed by 1 day recovery. As with myc-p62 (FIG. 1C), p62-EGFP-expressing atg5$^{-/-}$ iBMK cells displayed persistent p62 aggregates that were induced during metabolic stress and recovery while atg5$^{+/+}$ iBMK cells were able to effectively prevent their accumulation (FIGS. 6B and 6C). Consistent with transient expression, stable p62-EGFP expression also activated the DNA damage response (γ-H2AX positive nuclei) during stress and recovery, suggesting that accumulation of p62 was sufficient for oxidative stress and DNA damage induction commonly observed with autophagy-deficiency under stress (FIGS. 6B and 6C).

One of the mechanisms by which cells progress to aneuploidy is by accumulation of supernumerary centrosomes leading to multipolar spindles and cell division abnormalities, a characteristic phenotype in stressed autophagy-deficient cells. To determine whether p62-EGFP expression was sufficient to induce this phenotype under metabolic stress, the frequency of centrosome and cell division abnormalities in EGFP or p62-EGFP expressing atg5$^{+/+}$ and atg5$^{-/-}$ iBMK cells were analyzed. Unstressed, EGFP-expressing atg5$^{-/-}$ iBMK cells showed a higher basal level of supernumerary centrosomes (more than 2 per cell) (15.4%) compared to atg5$^{+/+}$ cells (1%), and p62-EGFP expression increased the frequency of centrosome abnormalities in both atg5$^{-/-}$ (25.8%) as well as in atg5$^{+/+}$ (11.4%) iBMK cells. Following metabolic stress (3 days) and recovery (1 day), EGFP-expressing atg5$^{-/-}$ iBMK cells displayed increased centrosomal abnormalities (45.3%) compared to the marginal increase in atg5$^{+/+}$ iBMK cells (4.6%) which was further increased by p62-EGFP expression in the atg5$^{-/-}$ cells (78.5%) compared to the atg5$^{+/+}$ cells (15.4%), and caused multi-polar divisions at markedly higher frequency in atg5$^{-/-}$ (65.1%) compared to atg5$^{+/+}$ (17.9%) iBMK cells. In contrast, control cells had a more modest but higher frequency of multi-polar divisions in atg5$^{-/-}$ (19.8%), compared to atg5$^{+/+}$ (1.8%) cells where p62 was progressively eliminated through autophagy. These observations suggested that p62 accumulation was sufficient for ROS and DNA damage response induction under metabolic stress and led to the cell division abnormalities and genomic instability in autophagy-defective cells. Indeed, RNAi-mediated knockdown of p62 during metabolic stress (3 days), reduced DNA damage induction in autophagy-deficient beclin1$^{+/-}$ and atg5$^{-/-}$ iBMK cells, further suggesting that the impairment of p62 elimination was the cause of DNA damage response activation (FIGS. 6D-6F).

Example 7 p62 Promotes Tumorgenesis of Autophagy-Defective Cells

Since accumulation of p62 is a pronounced phenotype of tissues and tumors from autophagy-deficient mice and some human cancers, the possibility was investigated that it was capable of promoting tumor growth. To this end, independently derived apoptosis-deficient atg5$^{+/+}$ and atg5$^{-/-}$ iBMK cell lines expressing comparable levels of EGFP or p62-EGFP (FIG. 7A) were assessed for their tumorigenic potential. p62-EGFP expression in atg5$^{+/+}$ iBMK cell lines did not substantially increase tumor growth (FIG. 7B). In contrast, p62-EGFP expression in atg5$^{-/-}$ cells dramatically increased the rate of tumor growth compared to EGFP-expressing atg5$^{-/-}$ controls (FIGS. 7B-7D). By optical imaging, tumors from p62-EGFP expressing atg5$^{-/-}$ cells were uniformly fluorescent indicating that the p62 fusion protein was expressed throughout the tumors (FIG. 7D). Fluorescence and histological analysis of EGFP-expressing atg5$^{-/-}$ tumor sections revealed diffuse cytoplasmic EGFP localization and uniformly sized nuclei with occasional appearance of tumor giant cells (FIG. 7E, H&E). In contrast, p62-EGFP-expressing atg5$^{-/-}$ tumors showed dramatic p62 aggregate accumulation (FIG. 7E, lower left panel), and numerous pleomorphic tumor cells with heterochromatic, giant nuclei by H&E staining (FIG. 7E), indicative of polyploidy and aneuploidy. Consistent with this, persistent p62 accumulation in p62-EGFP expressing atg5$^{-/-}$ tumors was also associated with markedly elevated DNA damage response induction (γ-H2AX staining) compared to EGFP-expressing atg5$^{-/-}$ tumors (p<0.005, t-test) (FIG. 7E), suggesting that inability to clear the p62 through autophagy promoted tumor growth by elevating DNA damage and genomic instability.

The results suggest that metabolic stress increases the demand for protein and organelle turnover by autophagy, and autophagy defects lead to induction and persistence of p62, which is sufficient to elevate oxidative stress, DNA damage, genomic instability and tumor progression. In autophagy-competent cells, p62 is progressively degraded through autophagy, minimizing oxidative stress and DNA damage (see model in FIG. 7F). These results thus indicate a role for autophagy in tumor suppression by damage mitigation under metabolic stress by eliminating p62.

Example 8

A cell-based screen utilizes apoptosis-defective bax$^{-/-}$ bak$^{-/-}$ immortal baby mouse kidney epithelial (iBMK) cells stably expressing the autophagosome marker EGFP-LC3 (D3-EGFP-LC3) (Degenhardt, K., Mathew, R., Beaudoin, B., Bray, K., Anderson, D., Chen, G., Mukherjee, C., Shi, Y., Gelinas, C., Fan, Y., et al., (2006), *Cancer Cell* 10, 51-64). Autophagy promotes tumor cell survival and restricts necrosis, inflammation, and tumorigenesis. Under normal growth conditions EGFP-LC3 is diffusely localized, and within 24 hours of metabolic stress in vitro and in tumors in vivo, 80-90% of the cells display membrane translocation and punctate localization of EGFPLC3 in autophagosomes. Deficiency in Bax and Bak produces a profound defect in apoptosis, allowing autophagy induction under stress without activating the apoptotic response. Genetic inactivation of autophagy (loss of or down regulation of Beclin1, Atg5 or Atg7) prevents relocalization of EGFP-LC3, which remains diffuse. Although inhibition of autophagy impairs survival to metabolic stress, the defect in apoptosis permits survival sufficiently to clearly reveal autophagy inhibition.

The apoptosis-defective iBMK cell line D3 stably expressing the autophagosome marker EGFPLC3 is utilized to monitor EGFP-LC3 translocation to autophagosomes in response to metabolic stress. Compounds and shRNAs that interfere with or promote autophagy induction are identified and validated. The autophagy-defective beclin1$^{+/-}$ EGFPLC3 iBMK cell line provides a negative control for autophagosome formation in metabolic stress. HCQ treated D3-EGFP-LC3 cells serve as a positive control for blockage of flux through the autophagic pathway, resulting in increased autophagosome accumulation.

Figure 8:
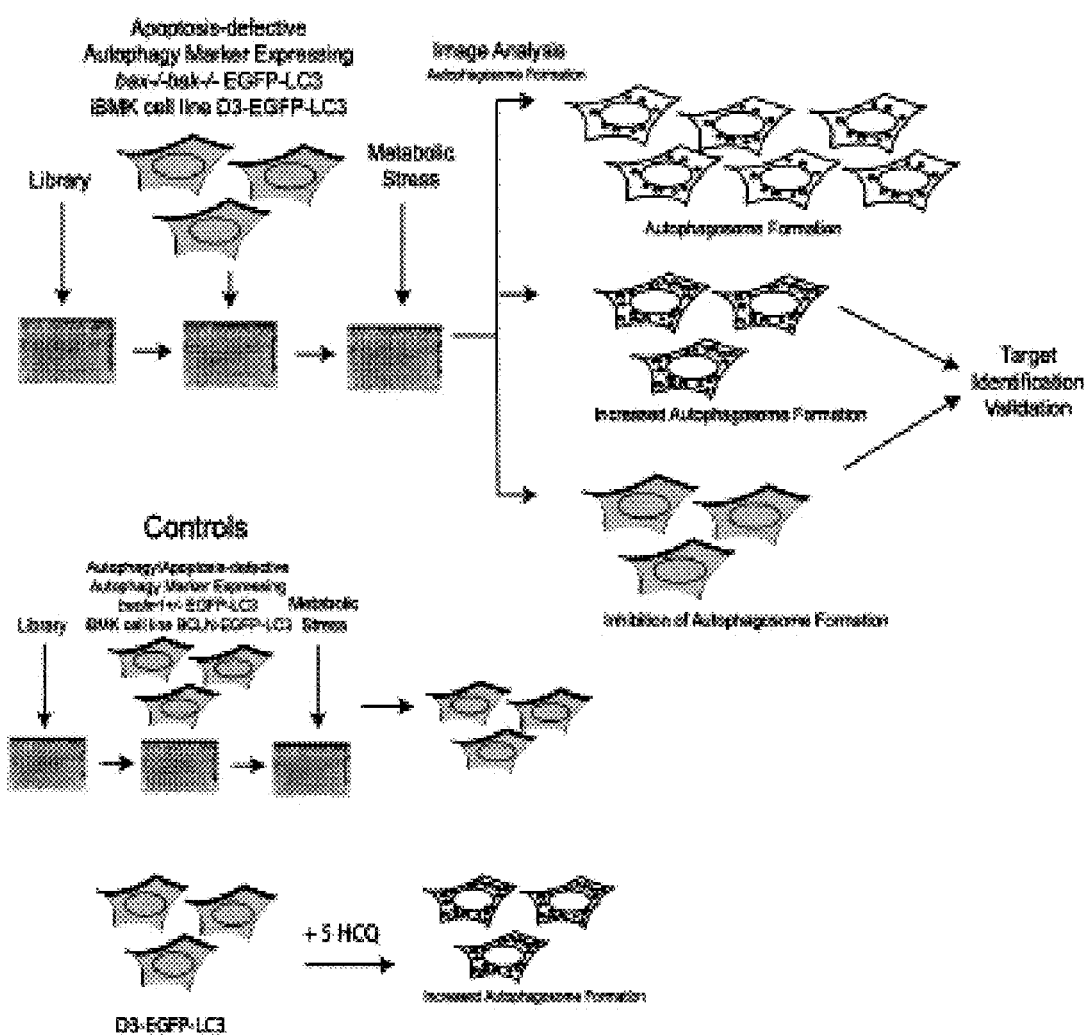
FIG. 8 illustrates a cell-based screen for autophagy inhibitors.

This screen is used to identify inhibitors of EGFP-LC3 membrane translocation (resulting in no autophagosome formation) as well as inhibitors of autophagosome trafficking, or lysosome fusion and acidification (such as HCQ), the subsequent stages of the autophagy pathway. The latter manifests as larger and more abundant GFP-LC3 decorated autophagosomes throughout the cell due to inhibition of flux through the pathway. Known autophagy inhibitors are included in the assay as a control for blockage of autophagy flux (FIGS. 12 and 8).

The shRNA screen is used to identify gene products that are important for metabolic stress-mediated autophagy induction that may be candidates for anti-cancer drug discovery targeting the autophagy pathway. The small molecule screen is used to identify compounds that are sufficient to disrupt the autophagic response to metabolic stress. The targets of these compounds are determined in subsequent validation studies.

Example 9

Figure 9:
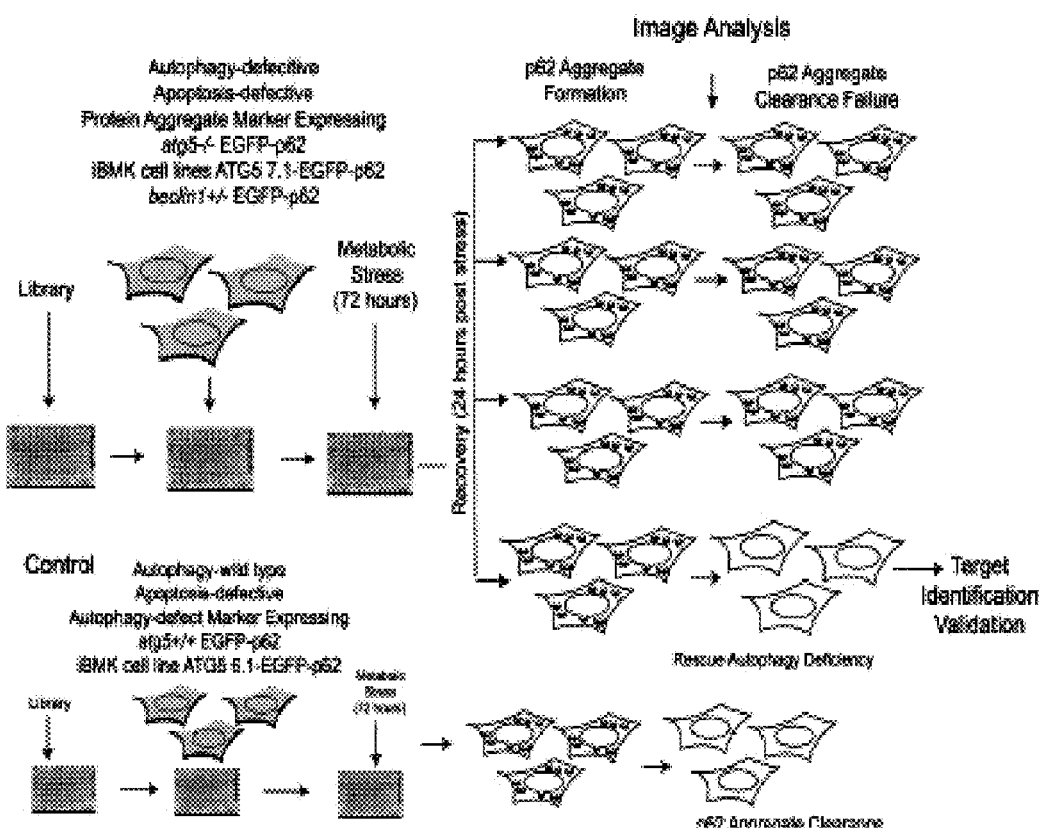
FIG. 9 illustrates a cell-based screen for rescue of autophagy defect and p62 protein aggregate accumulation in response to metabolic stress.
Figure 10:
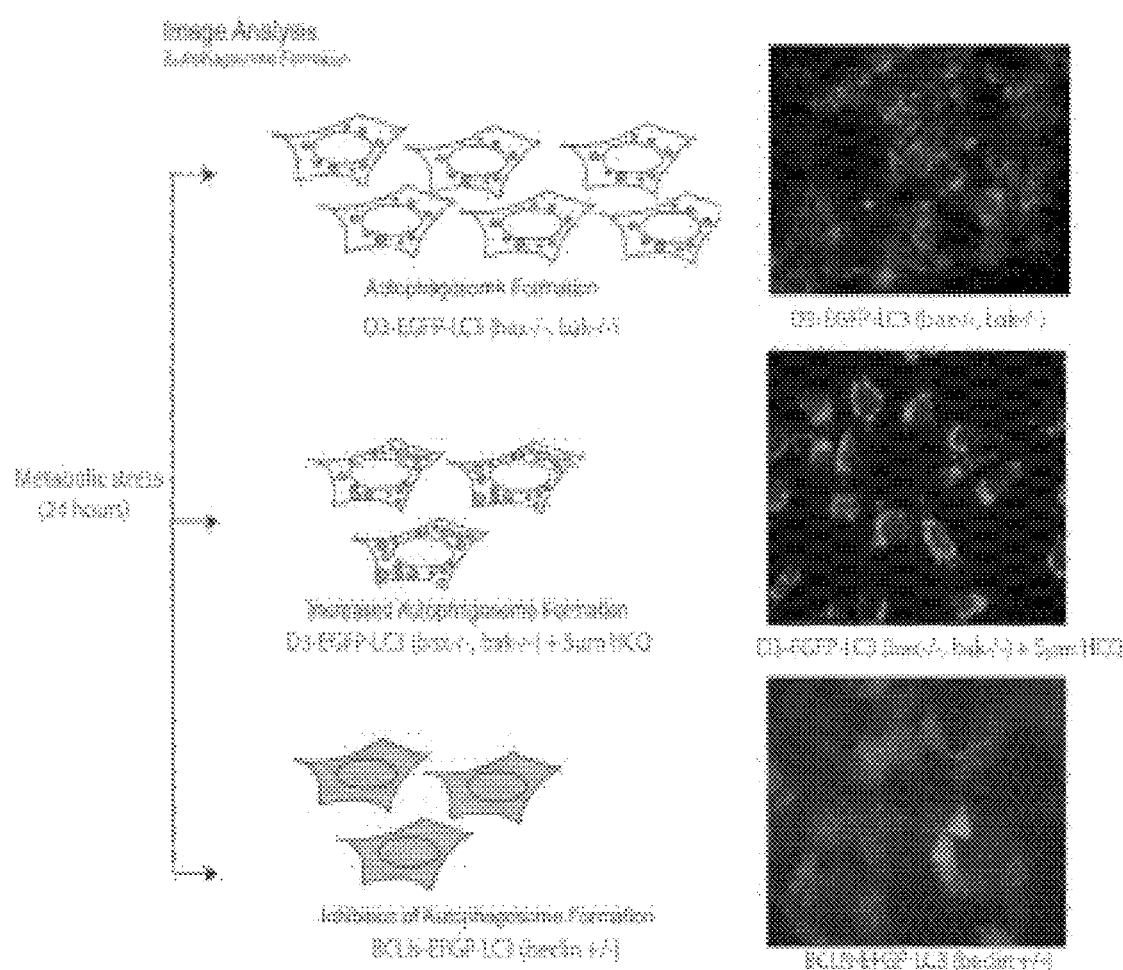
FIG. 10 illustrates reference images for a cell-based screen for inhibitors of autophagy.
Figure 11:
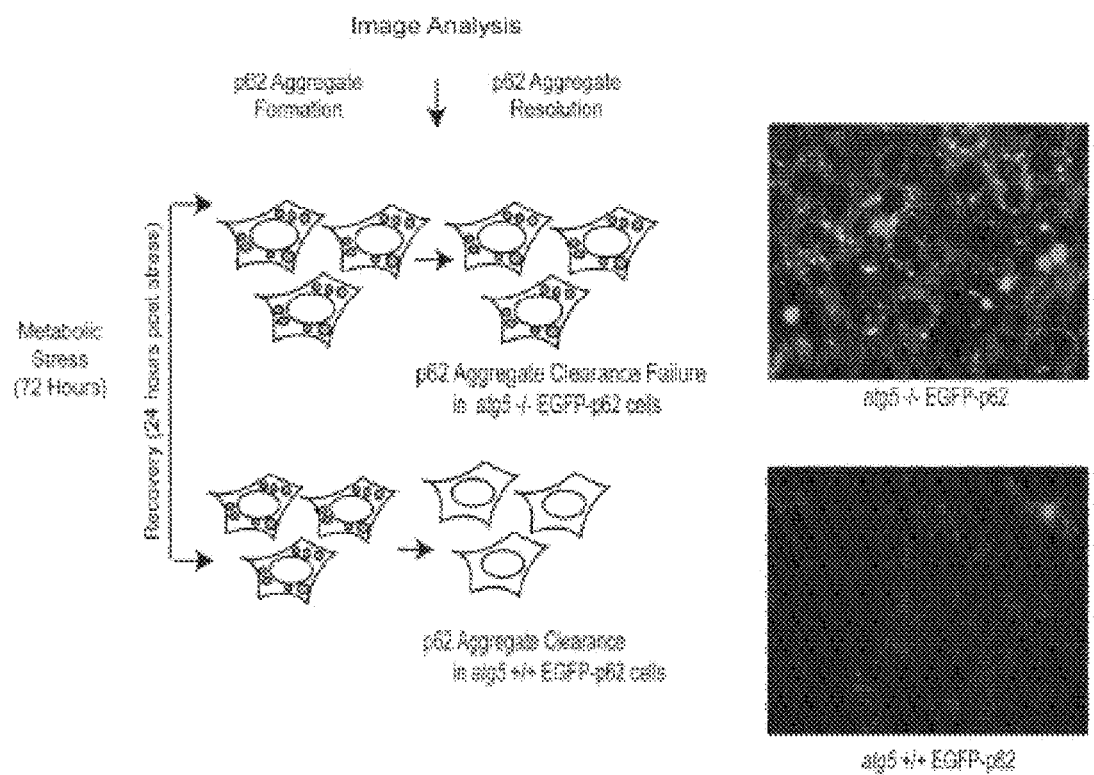
FIG. 11 illustrates reference images for a cell-based screen for autophagy promoters.

A cell-based screen utilizes autophagy defective atg5$^{-/-}$ and beclin1$^{+/-}$ iBMK cells (Mathew et al., 2007b) stably expressing EGFP-p62 (R. Mathew, C. M. Karp, B. Beaudoin, N. Vuong, G. Chen, H.-Y. Chen, K. Bray, A. Reddy, G. Bhanot, C. Gelinas, R. S. DiPaola, V. Karantza-Wadsworth, E. White, (2009), Autophagy suppresses tumorigenesis through elimination of p62, *Cell* 137, 1062-1075). p62 accumulates and aggregates in response to metabolic stress and requires autophagy for degradation. In shRNA screens, genes are identified where inactivation compensates for defective autophagy and restores p62 protein turnover (FIG. 9). Similarly, small molecule screens identify compounds that compensate for or restore functional autophagy by measuring the elimination of p62 aggregates. Both the beclin1$^{+/-}$ and atg5$^{-/-}$ autophagy-defective cells are screened in this assay, as fundamentally different mechanisms may govern compensation for a haploinsufficient and a null defect, respectively.

The autophagy-defective atg5$^{-/-}$ and beclin1$^{+/-}$ iBMK cell lines stably expressing EGFP-p62 accumulate p62-containing protein aggregates under stress, which fail to be cleared following recovery. Those shRNAs or small molecules that facilitate p62 aggregate clearance, compensating for defective autophagy, are identified and subjected to future validation. The autophagy wild type atg5$^{+/+}$ iBMK cell line stably expressing EGFP-p62 that effectively clears p62 aggregates following stress is used as a positive control. mTOR inhibitors and an mTOR-independent stimulator of autophagy, trehalose, are tested as a potential positive control for p62 elimination in atg5$^{-/-}$ or beclin1$^{+/-}$ cells.

While not wishing to be bound by any theory or theories of operation, evidence suggests that promoting autophagy and the clearance of misfolded proteins can greatly mitigate disease progression. The cell-based screens described herein may be used to screen for genes where down regulated expression suppresses metabolic stress-mediated p62 accumulation in autophagy-defective atg5$^{-/-}$ and beclin1$^{+/-}$ cells. These genes are expected to be therapeutic targets for small molecule inhibitors for prevention and/or treatment of diseases including, but not limited to, neurodegeneration, liver disease and cancer. Additionally, chemical libraries may be screened for compounds that can restore autophagy and result in p62 aggregate elimination in well-characterized autophagy-deficient cell lines.

The terms and expressions which have been employed are used as terms of descriptions and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush group or other grouping of alternatives, those skilled in the art will recognize that the invention is also thereby described in terms of any individual member or subgroup of members of the Markush group or other group.

The disclosures of each patent, patent application and publication cited or described in this document are hereby incorporated herein by reference, in their entireties.

What is claimed is:

1. A cell line comprising an autophagy-defective cell that stably expresses Sequestosome 1 (p62) protein linked to a label molecule.

2. The cell line of claim 1 wherein the cell expresses Enhanced Green Fluorescent Protein (EGFP)-Sequestosome 1 (p62).

3. The cell line of claim 1 wherein the cell has reduced expression of one or more genes selected from the group consisting of Beclin1, Atg5, and Atg7.

4. The cell line of claim 1 wherein the cell is apoptosis-defective.

5. The cell line of claim 1 wherein the cell is a mouse cell.

6. The cell line of claim 1 wherein the cell is an immortalized baby mouse kidney cell.

7. A method for identifying stimulators of autophagy comprising the steps of:
(A) contacting the test cell of claim 1 expressing a marker of protein aggregation with a compound;
(B) subjecting the cell to metabolic stress;
(C) performing analysis on the test cell to determine the level of the marker; and
(D) comparing the level of the marker in the test cell with that of a control cell not contacted with said compound, wherein a lower level of aggregates comprising the marker in the test cell compared to that demonstrated by the control cell not contacted with said compound indicates that the compound is capable of stimulating autophagy.

8. The method of claim 7 wherein the test cell is apoptosis-defective.

9. The method of claim 7 wherein the test cell is an immortalized baby mouse kidney cell.

* * * * *